United States Patent
Garbuzova-Davis et al.

(10) Patent No.: US 12,144,832 B1
(45) Date of Patent: Nov. 19, 2024

(54) PLASMA DERIVED FROM HUMAN UMBILICAL CORD BLOOD FOR THE TREATMENT OF NEURODEGENERATIVE DISORDERS

(71) Applicant: University of South Florida, Tampa, FL (US)

(72) Inventors: Svitlana Garbuzova-Davis, Tampa, FL (US); Jared Carl Ehrhart, Tampa, FL (US); Paul R. Sanberg, Spring Hill, FL (US)

(73) Assignees: University of South Florida, Tampa, FL (US); Saneron CCEL Therapeutics, Inc., Tampa, FL (US)

( * ) Notice: Subject to any disclaimer, the term of this patent is extended or adjusted under 35 U.S.C. 154(b) by 0 days.

(21) Appl. No.: 18/134,722

(22) Filed: Apr. 14, 2023

Related U.S. Application Data

(60) Division of application No. 16/655,506, filed on Oct. 17, 2019, now Pat. No. 11,628,190, which is a (Continued)

(51) Int. Cl.
*A61K 35/51* (2015.01)
*A61P 25/28* (2006.01)
*C12N 5/0775* (2010.01)

(52) U.S. Cl.
CPC .............. *A61K 35/51* (2013.01); *A61P 25/28* (2018.01); *C12N 5/0665* (2013.01)

(58) Field of Classification Search
CPC ........ A61K 35/51; C12N 5/0665; A61P 25/28
See application file for complete search history.

(56) References Cited

U.S. PATENT DOCUMENTS

| | | | | |
|---|---|---|---|---|
| 6,194,207 B1 * | 2/2001 | Bell | ..................... | C12N 5/0636 |
| | | | | 435/377 |
| 8,282,931 B2 * | 10/2012 | Alitalo | ................... | A61P 13/00 |
| | | | | 424/185.1 |

(Continued)

OTHER PUBLICATIONS

Yan Ding, Hua Yang, Jing Bo Feng, Ying Qiu, Dong Sheng Li and Yi Zeng, Human umbilical cord-derived MSC culture: the replacement of animal sera with human cord blood plasma, 2013, In Vitro Cell Dev Biol—Animal, vol. 49, pp. 771-777 (Year: 2013).*

(Continued)

*Primary Examiner* — David W Berke-Schlessel
*Assistant Examiner* — Trent R Clarke
(74) *Attorney, Agent, or Firm* — Michele L. Lawson; Smith & Hopen, P.A.

(57) ABSTRACT

A method of treating neurodegenerative diseases using hUCB plasma is presented herein. hUCB plasma attenuated the hyperactive response (Group III) and potentiated the normal response in Group I ALS patients, but did not alter that of the non-responders to PHA (Group II). The elevated activity of caspase 3/7 observed in the MNCs from ALS patients was significantly reduced by hUCB plasma treatment. The ability of hUCB plasma to modulate the mitogen cell response and reduce caspase activity suggest that the use of hUCB plasma alone, or with stem cells, may prove useful as a therapeutic in ALS patients. hUCB plasma was shown to increase therapeutic efficacy of MNCs as well as decrease apoptosis of MNCs. The cytokine profile of hUCB plasma supports its usefulness as a sole therapeutic as well as an additive to MNCs.

3 Claims, 21 Drawing Sheets

Related U.S. Application Data continuation-in-part of application No. 15/250,239, filed on Aug. 29, 2016, now Pat. No. 11,007,230.

(60) Provisional application No. 62/211,478, filed on Aug. 28, 2015.

(56) References Cited

U.S. PATENT DOCUMENTS

| | | | |
|---|---|---|---|
| 2002/0151680 A1* | 10/2002 | Alitalo | A61K 31/7052 530/350 |
| 2002/0164667 A1* | 11/2002 | Alitalo | C07K 14/71 424/1.49 |
| 2004/0203142 A1* | 10/2004 | Rai | C12N 5/0647 435/372 |
| 2005/0032697 A1* | 2/2005 | Alitalo | A61K 38/1866 514/8.1 |
| 2005/0059152 A1* | 3/2005 | Tanavde | C12N 5/0663 435/372 |
| 2009/0004661 A1* | 1/2009 | Shetty | C12N 5/0619 435/6.14 |
| 2011/0262393 A1* | 10/2011 | Yang | A61P 25/02 435/375 |
| 2013/0236425 A1* | 9/2013 | Laughlin | A61K 35/28 424/93.7 |
| 2015/0329827 A1* | 11/2015 | Young | C12N 5/0607 435/395 |
| 2017/0327792 A1* | 11/2017 | Mouzannar | A61L 27/3895 |

OTHER PUBLICATIONS

Kim et al., Ex Vivo Expansion of Human Umbilical Cord Blood-Derived T-Lymphocytes with Homologous Cord Blood Plasma, 2005, Tohoku J. Exp. Med., vol. 205, pp. 115-122 (Year: 2005).*

Lan Huang, Paul J. Critser, Brenda R. Grimes and Mervin C. Yoder, Human Umbilical Cord Blood Plasma Can Replace Fetal Bovine Serum (FBS) for in vitro Expansion of Functional Human Endothelial Colony Forming Cells (ECFCs), 2011, Cytotherapy, vol. 13, No. 6, pp. 712-721 (Year: 2011).*

\* cited by examiner

FIG. 16A-J

TABLE 1 Cytokine and growth factor profiles in cord blood plasma and adult blood plasma/serum

| A. Cytokine profile (pg/mL) | | | B. Growth factor profile (pg/mL) | | |
|---|---|---|---|---|---|
| Cytokine | CBP | ABP/S | Growth factor | CBP | ABP/S |
| IL-1β | 0.97 ± 0.14 | 1.24 ± 0.19 | VEGF | 7.23 ± 0.28** | 2.94 ± 0.11 |
| IL-2 | 0.93 ± 0.05** | 2.29 ± 0.27 | G-CSF | 57.89 ± 2.26* | 46.22 ± 0.52 |
| IL-4 | 5.40 ± 0.28 | 6.05 ± 0.23 | EGF | 11.00 ± 0.41** | 4.64 ± 0.13 |
| IL-5 | 1.17 ± 0.07** | 1.93 ± 0.22 | FGF Basic | 6.07 ± 0.18** | 2.35 ± 0.12 |
| IL-6 | 0.64 ± 0.07** | 1.20 ± 0.17 | | | |
| IL-8 | 13.02 ± 1.22** | 2.98 ± 0.79 | | | |
| IL-10 | 1.64 ± 0.06 | 1.91 ± 0.14 | | | |
| IFN-γ | 0.57 ± 0.08** | 1.41 ± 0.21 | | | |
| TNF-α | 1.23 ± 0.07** | 2.77 ± 0.25 | | | |
| GM-CSF | 1.91 ± 0.26** | 4.46 ± 0.15 | | | |

FIG. 17

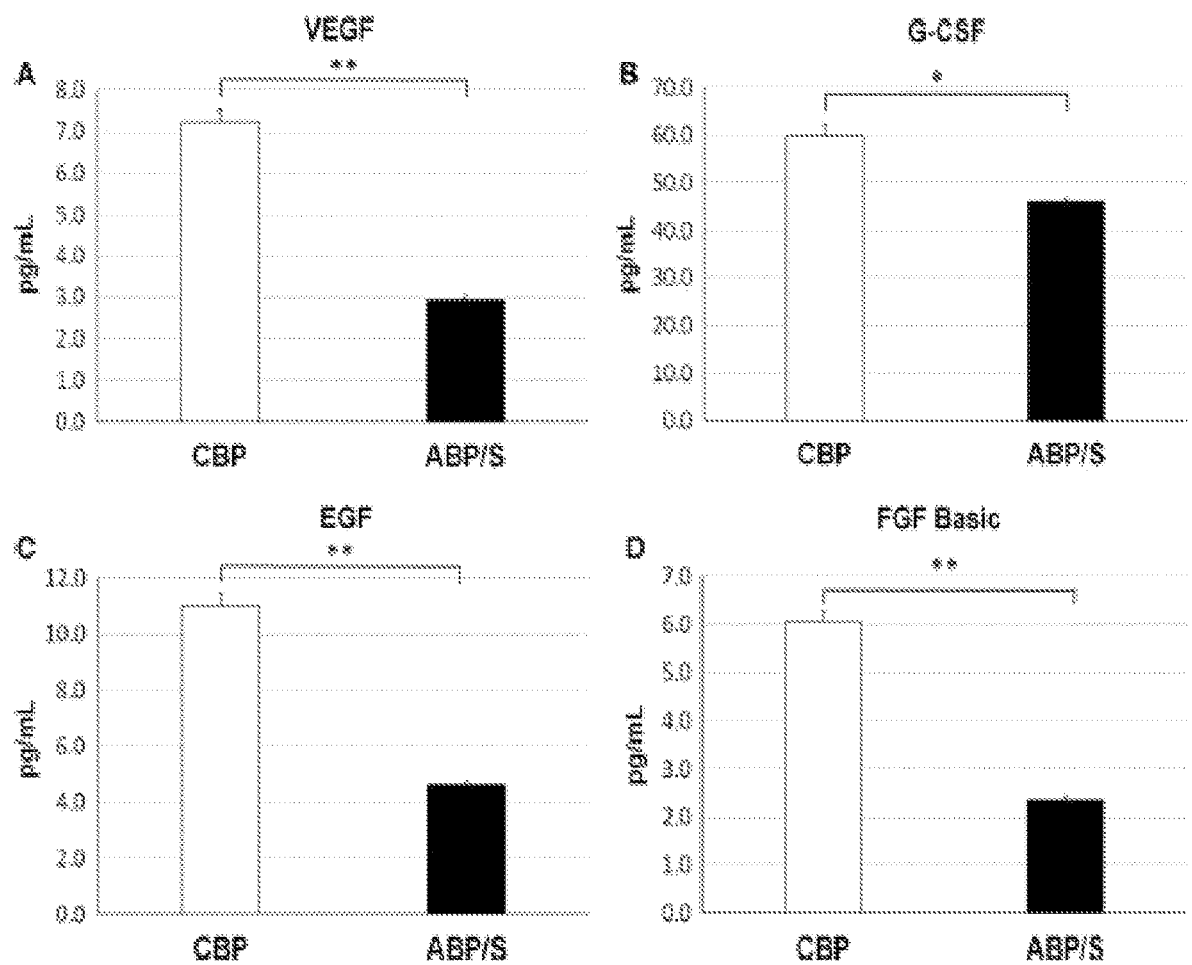
FIG. 18A-D

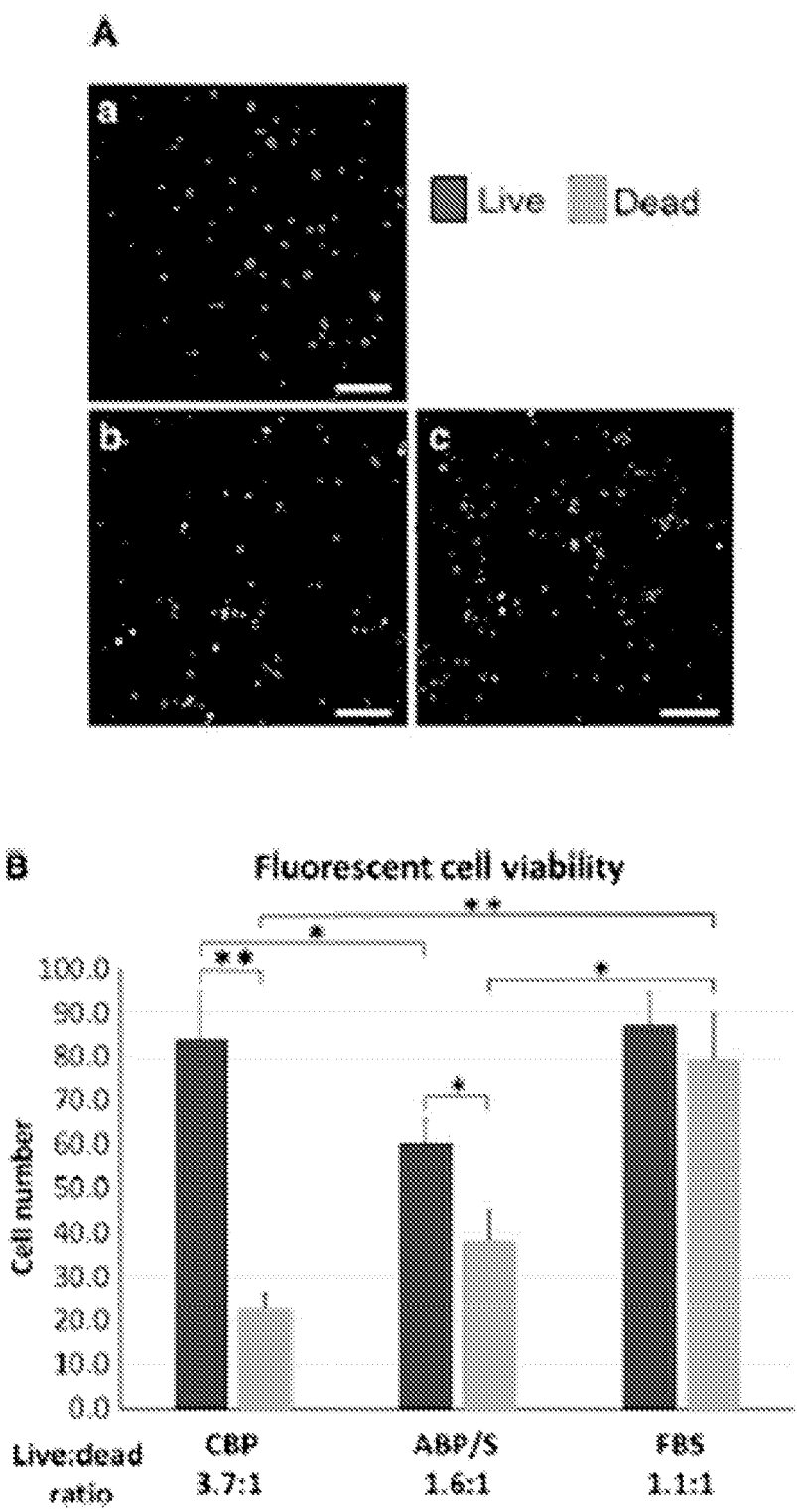
FIG. 19A-B

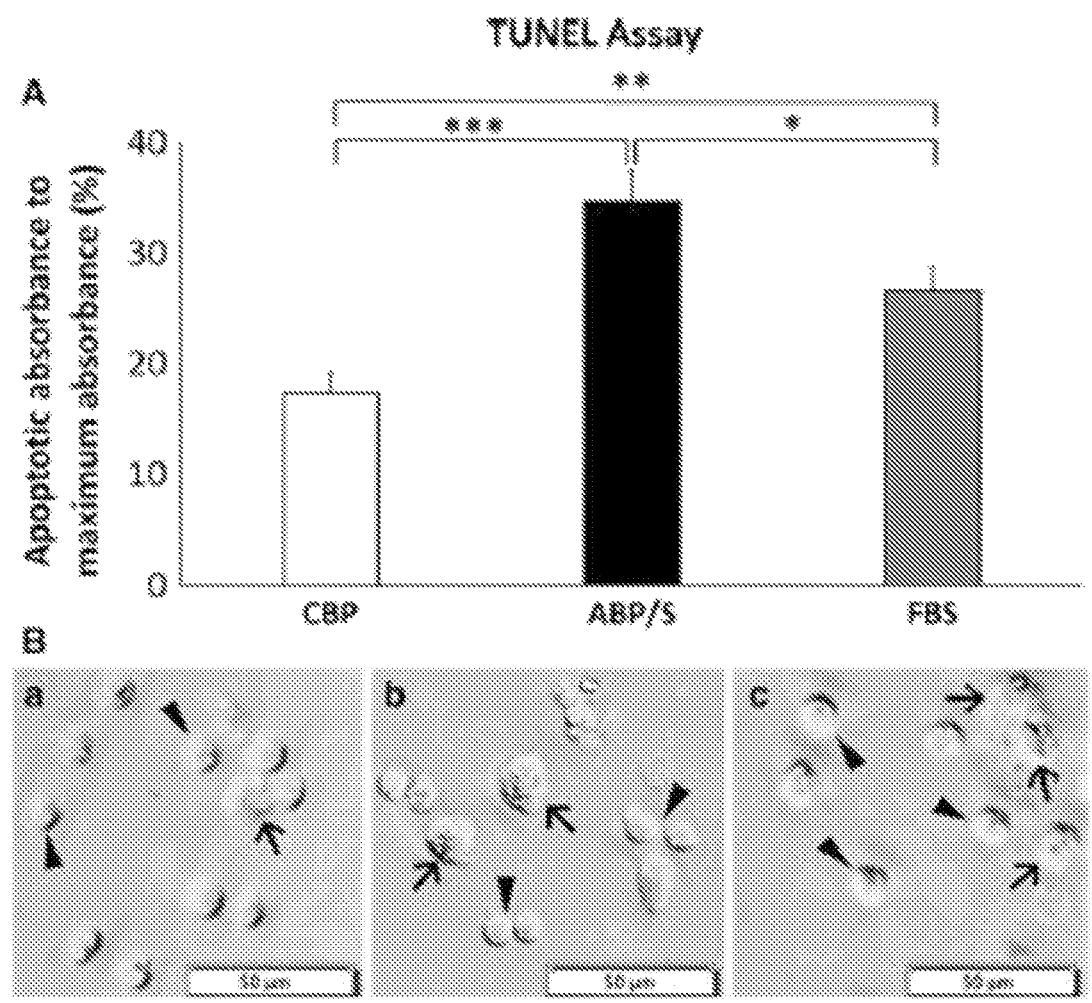
FIG. 20A-B

PLASMA DERIVED FROM HUMAN UMBILICAL CORD BLOOD FOR THE TREATMENT OF NEURODEGENERATIVE DISORDERS

CROSS REFERENCE TO RELATED APPLICATIONS

This application is a divisional of and claims priority to U.S. Nonprovisional application Ser. No. 16/655,506, entitled "Plasma Derived from Human Umbilical Cord Blood for the Treatment of Neurodegenerative Disorders", filed Oct. 17, 2019, which is a continuation in part of and claims priority to currently pending U.S. Nonprovisional application Ser. No. 15/250,239, now U.S. Pat. No. 11,007,230, entitled "Plasma Derived from Human Umbilical Cord Blood for the Treatment of Neurodegenerative Disorders", filed Aug. 29, 2016, which claims priority to U.S. Provisional Application No. 62/211,478, entitled "Plasma Derived from Human Umbilical Cord Blood for the Treatment of Neurodegenerative Disorders", filed Aug. 28, 2015, each of which is incorporated herein by reference.

FIELD OF INVENTION

This invention relates to treating neuronal diseases. Specifically, the invention addresses treating neurodegenerative diseases, and/or neuro-inflammatory diseases using cord blood-derived plasma.

BACKGROUND OF THE INVENTION

Amyotrophic Lateral Sclerosis (ALS)

Amyotrophic lateral sclerosis (ALS) is a progressive degenerative disease involving both upper and lower motor neuron damage in the spinal cord and brain. This disease clinically manifests as muscular weakness and atrophy, which lead to paralysis and death of patients by respiratory failure within 3 to 5 years (Rowland & Shneider, Amyotrophic lateral sclerosis. N. Engl. J. Med. 344(22):1688-1700; 2001). Most cases of ALS are sporadic; the familial (FALS), or genetically linked, form of ALS represents only 10 to 13 percent of all cases (Fiszman, et al., Cu/Zn superoxide dismutase activity at different ages in sporadic amyotrophic lateral sclerosis. J. Neurol. Sci. 162(1):34-37; 1999; Pramatarova, et al., Identification of new mutations in the Cu/Zn superoxide dismutase gene of patients with familial amyotrophic lateral sclerosis. Am. J. Hum. Genet. 56(3):592-596; 1995). About 20% of FALS cases are the result of mutations in the gene for Cu/Zn superoxide dismutase (SOD1) that are associated with a decrease in SOD1 activity. Over 140 different SOD1 gene mutations have been reported (Andersen, Amyotrophic lateral sclerosis associated with mutations in the CuZn superoxide dismutase gene. Curr. Neurol. Neurosci. Rep. 6(1):37-46; 2006). Available treatments for this disease lack the capacity to arrest disease progression or repair motor neuron function. Cell therapy may be a promising new treatment for ALS.

Human umbilical cord blood (hUCB) may be preferable to other cell sources such as bone marrow due to hUCB cells' low pathogenicity and immune immaturity. The mononuclear cell fraction from human hUCB (MNC hUCB) is relatively rich in multipotent progenitors and has extensive proliferation capacity (Mayani, & Lansdorp, Biology of human umbilical cord blood-derived hematopoietic stem/progenitor cells. Stem Cells 16(3):153-165; 1998; Todaro, et al., Hematopoietic progenitors from umbilical cord blood. Blood Purif. 18(2):144-147; 2000). A number of studies have shown that intravenously administering MNC hUCB (Saneron's proprietary fraction U-CORD-CELL™) into the jugular vein of G93A SOD1 mice delayed the progression of disease and prolonged lifespan, increased motor neuron survival in the cervical/lumbar spinal cord, decreased pro-inflammatory cytokines (interleukin [IL]-1α, IL-1β, tumor necrosis factor [TNF]-α), and restored leukocyte profiles in these mice (Garbuzova-Davis, et al., Multiple intravenous administrations of human umbilical cord blood cells benefit in a mouse model of ALS. PLoS One 7(2):e31254; 2012; Garbuzova-Davis, et al., Human umbilical cord blood treatment in a mouse model of ALS: optimization of cell dose. PLoS One 3(6):e2494; 2008; Garbuzova-Davis, et al., Intravenous administration of human umbilical cord blood cells in a mouse model of amyotrophic lateral sclerosis: distribution, migration, and differentiation. J. Hematother. Stem Cell Res. 12(3):255-270; 2003). While multiple interdependent factors may underlie the pathogenesis of ALS, increasing evidence supports a role for autoimmune mechanisms (Alexianu, The role of immune processes in amyotrophic lateral sclerosis pathogenesis. Rom. J. Neurol. Psychiatry 33(3-4):215-227; 1995; Appel, et al., Autoimmunity as an etiological factor in sporadic amyotrophic lateral sclerosis. Adv. Neurol. 68:47-57; 1995; Coban, et al., Serum anti-neuronal antibodies in amyotrophic lateral sclerosis. Int. J. Neurosci. 123(8):557-562; 2013; Niebroj-Dobosz, et al., Auto-antibodies against proteins of spinal cord cells in cerebrospinal fluid of patients with amyotrophic lateral sclerosis (ALS). Folia Neuropathol. 44(3):191-196; 2006; Pagani, et al., Autoimmunity in amyotrophic lateral sclerosis: past and present. Neurol. Res. Int. 2011:497080; 2011). MNC hUCB were hypothesized to provide neuroprotective and/or trophic effects for motor neurons by modulating the host immune inflammatory system through release of various growth or anti-inflammatory factors. Additionally, hUCB plasma (hUCBP) is a rich source of cytokines and other proteins such as insulin-like growth factor-1 (IGF-1), transforming growth factor (TGF)-β and vascular endothelial growth factor (VEGF) required for growth and survival of hematopoietic stem cells (Broxmeyer, et al., Commentary: a rapid proliferation assay for unknown co-stimulating factors in cord blood plasma possibly involved in enhancement of in vitro expansion and replating capacity of human hematopoietic stem/progenitor cells. Blood Cells 20(2-3):492-497; 1994; Kim, et al., Ex vivo expansion of human umbilical cord blood-derived T-lymphocytes with homologous cord blood plasma. Tohoku J. Exp. Med. 205(2):115-122; 2005; Lam, et al., Preclinical ex vivo expansion of cord blood hematopoietic stem and progenitor cells: duration of culture; the media, serum supplements, and growth factors used; and engraftment in NOD/SCID mice. Transfusion 41(12):1567-1576; 2001). Moreover, it has been shown that hUCB serum contains more neurotrophic factors (substance P, IGF-1, nerve growth factor [NGF]) compared to the peripheral blood serum effectively used for the treatment of the persistent corneal epithelial defects (Vajpayee, et al., Evaluation of umbilical cord serum therapy for persistent corneal epithelial defects. Br. J. Ophthalmol. 87(11):1312-1316; 2003), neurotrophic keratitis (Yoon, et al., Application of umbilical cord serum eyedrops for the treatment of neurotrophic keratitis. Ophthalmology 114(9):1637-1642; 2007), and recurrent corneal erosion (Yoon, et al., Application of umbilical cord serum eyedrops for recurrent corneal erosions. Cornea 30(7):744-748; 2011). hUCBP has also been used as a replacement for fetal bovine serum in in vitro studies including the expansion of endothelial colony forming cells (Huang, et al., Human umbilical cord blood plasma can replace fetal bovine serum for in vitro expansion of functional human endothelial colony-forming cells. Cytotherapy 13(6):712-721; 2011), mesenchymal stromal cells (MSCs) (Baba, et al., Osteogenic potential of human umbilical cord-derived mesenchymal stromal cells cultured with umbilical cord blood-derived auto serum. J. Craniomaxillofac. Surg. 40(8):768-772; 2012; Ding, et al., Human umbilical cord-derived MSC culture: the replacement of animal sera with human cord blood plasma. In Vitro Cell. Dev. Biol. Anim. 49(10):771-777; 2013), T cells (Kim, et al., Ex vivo expansion of human umbilical cord blood-derived T-lymphocytes with homologous cord blood plasma. Tohoku J. Exp. Med. 205(2):115-122; 2005), and dental stem cells (Lee, et al., The effects of platelet-rich plasma derived from human umbilical cord blood on the osteogenic differentiation of human dental stem cells. In Vitro Cell. Dev. Biol. Anim. 47(2):157-164; 2011), demonstrating that it can exert a favorable influence on stem cells. These results suggest that hUCBP may be effective as an additive to, or substitute for, cells in developing clinically useful protocols for cell-based ALS therapies. Including hUCBP with hUCB cells may add significant therapeutic benefits and plasma alone may also be a useful treatment approach.

The inventors determined the efficacy of hUCBP on the functional activity of lymphocytes from the peripheral blood of ALS patients. First, hematological profiles were analyzed in the peripheral blood of ALS patients. Second, the mitogen-induced proliferation response of MNCs isolated from the peripheral blood of ALS patients in vitro when cultured with hUCBP were investigated. Finally, the effect of hUCBP upon the apoptotic cell death response in ALS patients was examined.

Cord Blood Plasma

Cord blood plasma (CBP) is commonly obtained from human umbilical cord blood (hUCB) during cell isolation and has mainly been considered a waste product. However, the trophic effect of CBP has been shown in replacing standard serum during the expansion of hUCB-derived mesenchymal stem cells, human dental stem cells, hUCB-derived T-lymphocytes, or human endothelial colony-forming cells in vitro. (Ding Y, Yang H, Feng J B, et al. Human umbilical cord-derived MSC culture: the replacement of animal sera with human cord blood plasma. *In Vitro Cell Dev Biol Anim.* 2013; 49:771-777; Lee J-Y, Nam H, Park Y-J, et al. The effects of platelet-rich plasma derived from human umbilical cord blood on the osteogenic differentiation of human dental stem cells. *In Vitro Cell Dev Biol Anim.* 2011; 47:157-164; Kim Y-M, Jung M-H, Song H-Y et al. Ex vivo expansion of human umbilical cord blood-derived T-lymphocytes with homologous cord blood plasma. *Tohoku J Exp Med.* 2005; 205:115-122; Huang L, Critser P J, Grimes B R, Yoder M C. Human umbilical cord blood plasma can replace fetal bovine serum for in vitro expansion of functional human endothelial colony-forming cells. *Cytotherapy.* 2011; 13:712-721). Moreover, the therapeutic potential of CBP administration into rats modelling acute ischemic stroke was demonstrated by enhancement of neurogenesis and reduction of inflammation leading to significant post-stroke functional recovery. (Yoo J, Kim H-S, Seo J-J, et al. Therapeutic effects of umbilical cord blood plasma in a rat model of acute ischemic stroke. *Oncotarget.* 2016; 7:79131-79140). Also, tissue inhibitor of metalloproteinases, a plasticity-enhancing protein from CBP, has been found to promote restoration of hippocampal function and memory in aged 18 months old mice after CBP treatment. (Lee J-Y, Nam H, Park Y-J, et al. The effects of platelet-rich plasma derived from human umbilical cord blood on the osteogenic differentiation of human dental stem cells. *In Vitro Cell Dev Biol Anim.* 2011; 47:157-164; Castellano J M, Mosher K I, Abbey R J, et al. Human umbilical cord plasma proteins revitalize hippocampal function in aged mice. *Nature.* 2017; 544:488-492).

A recent study showed beneficial functional improvement in an Alzheimer's disease (AD) mouse model by injection of a specific fraction from cord blood serum compared to adult blood serum. (Habib A, Hou H, Mori T, et al. Human umbilical cord blood serum-derived α-secretase: functional testing in Alzheimer's disease mouse models. *Cell Transplant.* 2018). Additionally, umbilical cord serum has being effectively employed for the treatment of corneal defects and neurotrophic keratitis in humans. (Vajpayee R B, Mukerji N, Tandon R, et al. Evaluation of umbilical cord serum therapy for persistent corneal epithelial defects. *Br J Opthamol.* 2003; 87:1312-1316; Yoon K-C, Choi W, You I-C, Choi J. Application of umbilical cord serum eyedrops for recurrent corneal erosions. *Cornea.* 2011; 30:744-748; Yoon K-C, You I-C, Im S-K, et al. Application of umbilical cord serum eyedrops for the treatment of neurotrophic keratitis. *Opthamol.* 2007; 114:1637-1642).

In a relatively recent study, the inventors showed the ability of CBP to modulate mitogen-induced in vitro proliferation of mononuclear cells (MNC) isolated from the peripheral blood of amyotrophic lateral sclerosis (ALS) patients. (Eve D J, Ehrhart J, Zesiewicz T, et al. Plasma Derived From Human Umbilical Cord Blood Modulates Mitogen-Induced Proliferation of Mononuclear Cells Isolated From the Peripheral Blood of ALS Patients. *Cell Transplant.* 2016; 25:963-971). Interestingly, three distinct cell responses to the mitogenic factor phytohemagglutinin were noted, suggesting altered lymphocyte functionality in ALS patients. MNC responses were shown to be regulated by CBP treatment in vitro. Additionally, the apoptotic activity of MNCs isolated from ALS patients was significantly reduced by supplementing media with CBP. Thus, these study results have not only broadened the therapeutic application of CBP for ALS, but also further expanded its potential for treatment of other neurodegenerative disorders with immunological aspects.

It has been shown that CBP contains high amounts of various growth factors, such as vascular endothelial growth factor (VEGF), insulin-like growth factor-1 and transforming growth factor (TGF)-β, that are required for cell maintenance during hematopoiesis. (Kim Y-M, Jung M-H, Song H-Y, et al. Ex vivo expansion of human umbilical cord blood-derived T-lymphocytes with homologous cord blood plasma. *Tohoku J Exp Med.* 2005; 205:115-122; Lam A C, Li K, Zhang X B, et al. Preclinical ex vivo expansion of cord blood hematopoietic stem and progenitor cells: duration of culture; the media, serum supplements, and growth factors used; and engraftment in NOD/SCID mice. *Transfusion.* 2001; 41:1567-1576). Although CBP can exert a favorable effect on hematopoietic stem cells, whether CBP elicits therapeutic benefit as an additive to, or substitute for, cells must be determined before developing clinically relevant CBP-based therapies for various neurodegenerative diseases.

The inventors characterized the composition of factors in CBP derived from hUCB, which may mediate therapeutic benefit. First, cytokine and growth factor profiles were analyzed in the same CBP samples. Second, the efficacy of autologous CBP on MNC hUCB viability in vitro was investigated. Finally, the effect of autologous CBP upon the apoptotic MNC hUCB response in vitro was examined.

These study results provide a basis for further establishment of CBP as a self-contained therapeutic or as a supportive diluent for MNC hUCB infusion in treatment of neurodegenerative diseases.

SUMMARY OF THE INVENTION

Treatment of a neuromotor degenerative disease is disclosed herein. The treatment comprises identifying a patient suffering from a neuromotor degenerative disease, such as through use of the ALS Functional Rating Scale or ALS Functional Rating Scale or ALS Functional Rating Scale or ALS Functional Rating Scale-revised methods. As such, in some embodiments, the neuromotor degenerative disease is amyotrophic lateral sclerosis. The patient is administered plasma derived from umbilical cord blood. In specific variations of the invention the plasma derived from umbilical cord blood is derived from human umbilical cord blood.

Other embodiments of the invention include the treatment of a neurodegenerative disease such as Alzheimer's disease, Parkinson's disease, multiple sclerosis, ischemia, or traumatic brain injury by the administration of a therapeutically effective amount of human umbilical cord blood plasma or alternatively, a therapeutically effective amount of human umbilical cord blood plasma in combination with a therapeutically effective amount of human umbilical cord blood cells. In some embodiments, the human umbilical cord blood cells may be a mononuclear fraction thereof.

Optionally, plasma derived from umbilical cord blood is administered at about 10 ml/kg to about 20 ml/kg. As nonlimiting examples, the plasma derived from umbilical cord blood can be administered at 9 ml/kg, 9.25 ml/kg, 9.5 ml/kg, 9.75 ml/kg, 10 ml/kg, 10.25 ml/kg, 10.5 ml/kg, 10.75 ml/kg, 11 ml/kg, 11.25 ml/kg, 11.5 ml/kg, 11.75 ml/kg, 12 ml/kg, 12.25 ml/kg, 12.5 ml/kg, 12.75 ml/kg, 13 ml/kg, 13.25 ml/kg, 13.5 ml/kg, 13.75 ml/kg, 14 ml/kg, 14.1 ml/kg, 14.2 ml/kg, 14.3 ml/kg, 14.4 ml/kg, 14.5 ml/kg, 14.6 ml/kg, 114.7 ml/kg, 14.75 ml/kg, 14.8 ml/kg, 14.9 ml/kg, 15 ml/kg, 15.1 ml/kg, 15.2 ml/kg, 15.25 ml/kg, 15.3 ml/kg, 15.4 ml/kg, 15.5 ml/kg, 15.6 ml/kg, 15.7 ml/kg, 15.75 ml/kg, 15.8 ml/kg, 15.9 ml/kg, 16 ml/kg, 16.1 ml/kg, 16.2 ml/kg, 16.25 ml/kg, 16.3 ml/kg, 16.4 ml/kg, 16.5 ml/kg, 16.6 ml/kg, 16.7 ml/kg, 16.75 ml/kg, 16.8 ml/kg, 16.9 ml/kg, 17 ml/kg, 17.25 ml/kg, 17.5 ml/kg, 17.75 ml/kg, 18 ml/kg, 18.25 ml/kg, 18.5 ml/kg, 18.75 ml/kg, 19 ml/kg, 19.25 ml/kg, 19.5 ml/kg, 19.75 ml/kg, or 20 ml/kg.

Optionally, a therapeutic composition is administered with the plasma derived from umbilical cord blood. The therapeutic composition is riluzole, mesenchymal stem cells, umbilical cord blood cells, or a combination of the aforementioned compounds. In specific variations, the therapeutic composition is umbilical cord blood cells, and may be a mononuclear cell fraction of umbilical cord blood cells. In more specific variations, the composition is a composition of $CD34^+$ cells from the umbilical cord blood cells.

In specific variations, the umbilical cord blood cells are administered at about $1\times10^4$ to about $5\times10^7$ cells, about $1\times10^5$ to about $9\times10^6$ cells, about $2\times10^5$ to about $8\times10^6$ cells, or about $2\times10^5$ cells. Nonlimiting examples include $9\times10^3$ cells, $1.0\times10^4$ cells, $1.25\times10^4$ cells, $1.5\times10^4$ cells, $1.75\times10^4$ cells, $2.0\times10^4$ cells, $2.25\times10^4$ cells, $2.5\times10^4$ cells, $2.75\times10^4$ cells, $3.0\times10^4$ cells, $3.25\times10^4$ cells, $3.75\times10^4$ cells, $4.0\times10^4$ cells, $4.25\times10^4$ cells, $4.5\times10^4$ cells, $4.75\times10^4$ cells, $5.0\times10^4$ cells, $5.25\times10^4$ cells, $5.5\times10^4$ cells, $5.75\times10^4$ cells, $6.0\times10^4$ cells, $6.25\times10^4$ cells, $6.75\times10^4$ cells, $7.0\times10^4$ cells, $7.25\times10^4$ cells, $7.75\times10^4$ cells, $8.0\times10^4$ cells, $8.25\times10^4$ cells, $8.75\times10^4$ cells, $9.0\times10^4$ cells, $9.25\times10^4$ cells, $9.75\times10^4$ cells, $1.0\times10^5$ cells, $1.25\times10^5$ cells, $1.5\times10^5$ cells, $1.75\times10^5$ cells, $2.0\times10^5$ cells, $2.25\times10^5$, $2.5\times10^5$ cells, $2.75\times10^5$ cells, $3.0\times10^5$ cells, $3.25\times10^5$ cells, $3.75\times10^5$ cells, $4.0\times10^5$ cells, $4.25\times10^5$ cells, $4.5\times10^5$ cells, $4.75\times10^5$ cells, $5.0\times10^5$ cells, $5.25\times10^5$ cells, $5.5\times10^5$ cells, $5.75\times10^5$ cells, $6.0\times10^5$ cells, $6.25\times10^5$ cells, $6.75\times10^5$ cells, $7.0\times10^5$ cells, $7.25\times10^5$ cells, $7.75\times10^5$ cells, $8.0\times10^5$ cells, $8.25\times10^5$ cells, $8.75\times10^5$ cells, $9.0\times10^5$ cells, $9.25\times10^5$ cells, $9.75\times10^5$ cells, $1.0\times10^6$ cells, $1.25\times10^6$ cells, $1.5\times10^6$ cells, $1.75\times10^6$ cells, $2.0\times10^6$ cells, $2.25\times10^6$, $2.5\times10^6$ cells, $2.75\times10^6$ cells, $3.0\times10^6$ cells, $3.25\times10^6$ cells, $3.75\times10^6$ cells, $4.0\times10^6$ cells, $4.25\times10^6$ cells, $4.5\times10^6$ cells, $4.75\times10^6$ cells, $5.0\times10^6$ cells, $5.25\times10^6$ cells, $5.5\times10^6$ cells, $5.75\times10^6$ cells, $6.0\times10^6$ cells, $6.25\times10^6$ cells, $6.75\times10^6$ cells, $7.0\times10^6$ cells, $7.25\times10^6$ cells, $7.75\times10^6$ cells, $8.0\times10^6$ cells, $8.25\times10^6$ cells, $8.75\times10^6$ cells, and $9.0\times10^6$ cells.

Alternatively, the umbilical cord blood cells are administered at about $0.1\times10^6$ cells/kg to about $10\times10^8$ cells/kg, about $0.5\times10^6$ cells/kg to about $5\times10^8$ cells/kg, or about $1\times10^7$ cells/kg to about $2\times10^8$ cells/kg. Nonlimiting examples include $1.0\times10^5$ cells/kg, $1.25\times10^5$ cells/kg, $1.5\times10^5$ cells/kg, $1.75\times10^5$ cells/kg, $2.0\times10^5$ cells/kg, $2.25\times10^5$, $2.5\times10^5$ cells/kg, $2.75\times10^5$ cells/kg, $3.0\times10^5$ cells/kg, $3.25\times10^5$ cells/kg, $3.75\times10^5$ cells/kg, $4.0\times10^5$ cells/kg, $4.25\times10^5$ cells/kg, $4.5\times10^5$ cells/kg, $4.75\times10^5$ cells/kg, $5.0\times10^5$ cells/kg, $5.25\times10^5$ cells/kg, $5.5\times10^5$ cells/kg, $5.75\times10^5$ cells/kg, $6.0\times10^5$ cells/kg, $6.25\times10^5$ cells/kg, $6.75\times10^5$ cells/kg, $7.0\times10^5$ cells/kg, $7.25\times10^5$ cells/kg, $7.75\times10^5$ cells/kg, $8.0\times10^5$ cells/kg, $8.25\times10^5$ cells/kg, $8.75\times10^5$ cells/kg, $9.0\times10^5$ cells/kg, $9.25\times10^5$ cells/kg, $9.75\times10^5$ cells/kg, $1.0\times10^6$ cells/kg, $1.25\times10^6$ cells/kg, $1.5\times10^6$ cells/kg, $1.75\times10^6$ cells/kg, $2.0\times10^6$ cells/kg, $2.25\times10^6$, $2.5\times10^6$ cells/kg, $2.75\times10^6$ cells/kg, $3.0\times10^6$ cells/kg, $3.25\times10^6$ cells/kg, $3.75\times10^6$ cells/kg, $4.0\times10^6$ cells/kg, $4.25\times10^6$ cells/kg, $4.5\times10^6$ cells/kg, $4.75\times10^6$ cells/kg, $5.0\times10^6$ cells/kg, $5.25\times10^6$ cells/kg, $5.5\times10^6$ cells/kg, $5.75\times10^6$ cells/kg, $6.0\times10^6$ cells/kg, $6.25\times10^6$ cells/kg, $6.75\times10^6$ cells/kg, $7.0\times10^6$ cells/kg, $7.25\times10^6$ cells/kg, $7.75\times10^6$ cells/kg, $8.0\times10^6$ cells/kg, $8.25\times10^6$ cells/kg, $8.75\times10^6$ cells/kg, $9.0\times10^6$ cells/kg, $9.25\times10^6$ cells/kg, $9.75\times10^6$ cells/kg, $1.0\times10^7$ cells/kg, $1.25\times10^7$ cells/kg, $1.5\times10^7$ cells/kg, $1.75\times10^7$ cells/kg, $2.0\times10^7$ cells/kg, $2.25\times10^7$, $2.5\times10^7$ cells/kg, $2.75\times10^7$ cells/kg, $3.0\times10^7$ cells/kg, $3.25\times10^7$ cells/kg, $3.75\times10^7$ cells/kg, $3.8\times10^7$ cells/kg, $4.0\times10^7$ cells/kg, $4.25\times10^7$ cells/kg, $4.5\times10^7$ cells/kg, $4.75\times10^7$ cells/kg, $5.0\times10^7$ cells/kg, $5.25\times10^7$ cells/kg, $5.5\times10^7$ cells/kg, $5.75\times10^7$ cells/kg, $6.0\times10^7$ cells/kg, $6.25\times10^7$ cells/kg, $6.75\times10^7$ cells/kg, $7.0\times10^7$ cells/kg, $7.25\times10^7$ cells/kg, $7.75\times10^7$ cells/kg, $8.0\times10^7$ cells/kg, $8.25\times10^7$ cells/kg, $8.75\times10^7$ cells/kg, $9.0\times10^7$ cells/kg, $9.25\times10^7$ cells/kg, $9.75\times10^7$ cells/kg, $1.0\times10^8$ cells/kg, $1.25\times10^8$ cells/kg, $1.5\times10^8$ cells/kg, $1.75\times10^8$ cells/kg, $2.0\times10^8$ cells/kg, $2.25\times10^8$, $2.5\times10^8$ cells/kg, $2.75\times10^8$ cells/kg, $3.0\times10^8$ cells/kg, $3.25\times10^8$ cells/kg, $3.75\times10^8$ cells/kg, $4.0\times10^8$ cells/kg, $4.25\times10^8$ cells/kg, $4.5\times10^8$ cells/kg, $4.75\times10^8$ cells/kg, $5.0\times10^8$ cells/kg, $5.25\times10^8$ cells/kg, $5.5\times10^8$ cells/kg, $5.75\times10^8$ cells/kg, $6.0\times10^8$ cells/kg, $6.25\times10^8$ cells/kg, $6.75\times10^8$ cells/kg, $7.0\times10^8$ cells/kg, $7.25\times10^8$ cells/kg, $7.75\times10^8$ cells/kg, $8.0\times10^8$ cells/kg, $8.25\times10^8$ cells/kg, $8.75\times10^8$ cells/kg, $9.0\times10^8$ cells/kg, $9.25\times10^8$ cells/kg, $9.75\times10^8$ cells/kg, and $1.0\times10^9$ cells/kg.

BRIEF DESCRIPTION OF THE DRAWINGS

For a fuller understanding of the invention, reference should be made to the following detailed description, taken in connection with the accompanying drawings, in which:

FIG. 17 is a table (Table 1) depicting the levels of cytokines and growth factors presented as mean±SEM. CBP: Cord Blood Plasma; ABP/S: Adult Blood Plasma/Serum; Interleukin (IL): 10, 2, 4, 5, 6, 8, and 10; IFN-γ: Interferon-gamma; TNF-α: Tumor necrosis factor-alpha; GM-CSF: Granulocyte-macrophage colony stimulating factor; VEGF: Vascular endothelial growth factor; G-CSF: Granulocyte-colony stimulating factor, EGF: Epithelial growth factor; FGF Basic: Fibroblast growth factor basic. Significance of CBP vs. ABP/S denoted by: *P<0.05; **P<0.01.

FIG. 18A-D is a series of graphs depicting cord blood plasma growth factor profile. The levels of the growth factors were analyzed in CBP (n=20) and ABP/S (n=6) using a human growth factor multiplex assay in triplicate. Significantly higher concentrations of (A) VEGF, (B) G-CSF, (C) EGF and (D) FGF basic growth factors were detected in CBP vs. ABP/S. *P<0.05, **P<0.01

FIG. 19A-B are a series of images depicting viability of MNC hUCB in vitro. MNC hUCB (n=4 units) was cultured for 5 d in media supplemented with either autologous CBP, ABP/S, or FBS in duplicate. The cells were stained using the LIVE/DEAD Viability/Cytotoxicity assay to identify the viable (dark grey fluorescence) and non-viable cytotoxic (light grey fluorescence) cell populations from images totaling n=16-20/supplemental condition. (A) Confocal microscopy images demonstrated numerous viable (dark grey) MNC hUCB cultured with (Aa) CBP and (Ac) FBS supplements. Fewer viable cells were detected in culture supplemented with (Ab) ABP/S. Scale bar in Aa-Ac is 100 μm. (B) MNCs cultured with autologous CBP supplement showed significantly greater cell survival vs. ABP/S. Also, media supplemented with CBP showed significantly reduced numbers of dead (light grey) MNC hUCB compared to FBS. Cells supplemented in media with CBP had a greater live (dark grey)/dead (light grey) cell ratio compared to cultures that received ABP/S or FBS.*P<0.05, **P<0.01

FIG. 20A-B is a series of images depicting apoptotic activity of MNC hUCB in vitro. MNC hUCB (n=6 units) was cultured for 5 d in media supplemented with either autologous CBP, ABP/S, or FBS in duplicate. Apoptosis was detected by TUNEL assay. (A) MNCs cultured in autologous CBP showed a significantly lower percentage of apoptotic absorbance vs. cultures supplemented with ABP/S or FBS. Cells incubated with FBS also exhibited significantly lower absorbance of apoptotic activity compared to ABP/S. *P<0.05, P<0.01, *P<0.001. (B) Phase contrast images of MNC hUCB in vitro demonstrated a few cells with abnormal morphology displaying dislocated nuclei in cultures supplemented with (Ba) CBP compared to numerous morphologically damaged cells cultured with (Bb) ABP/S or (Bc) FBS, supporting apoptotic cell counts. Arrowheads indicate healthy cells with normal morphology. Arrows indicate cells with abnormal morphology. Scale bar in Ba-Bc is 50 μm

DETAILED DESCRIPTION OF THE PREFERRED EMBODIMENT

Figure 1A:
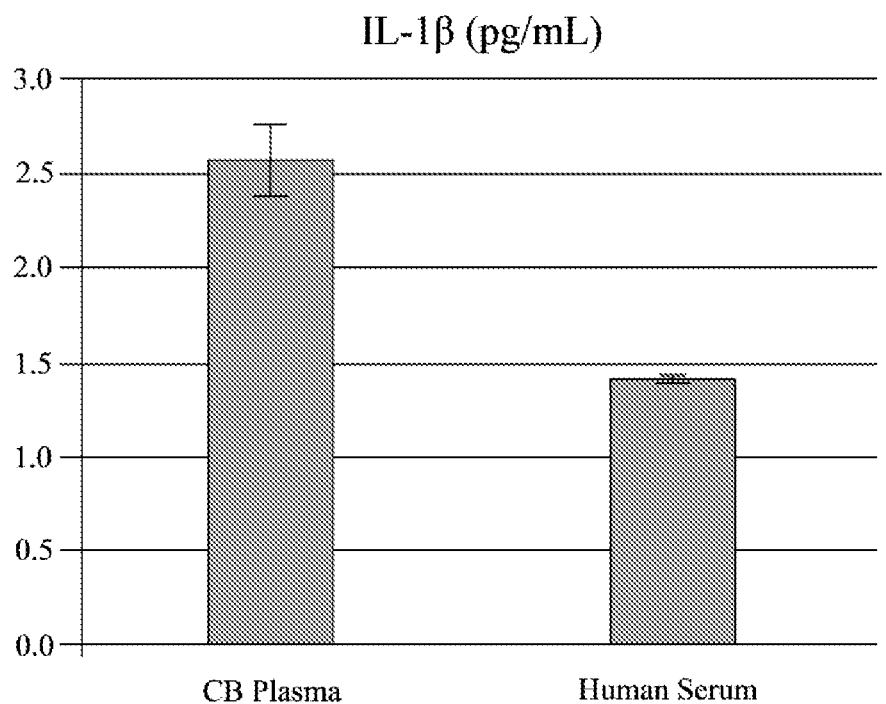
FIG. 1(A) is a graph showing the cytokine profile was assayed on plasma derived from human umbilical cord blood and human adult serum using an ultrasensitive human cytokine panel for IL-1β. Results are plotted as mean±SEM. Statistical significance was determined using two tailed t-tests (* p<0.001).
Figure 1B:
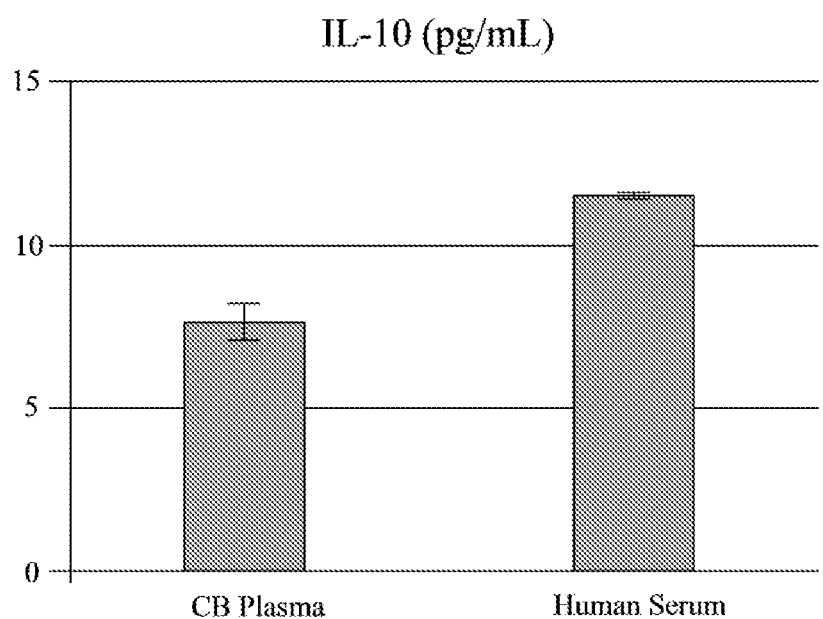
FIG. 1(B) is a graph showing the cytokine profile was assayed on plasma derived from human umbilical cord blood and human adult serum using an ultrasensitive human cytokine panel for IL-10. Results are plotted as mean±SEM. Statistical significance was determined using two tailed t-tests (* p<0.001).
Figure 1C:
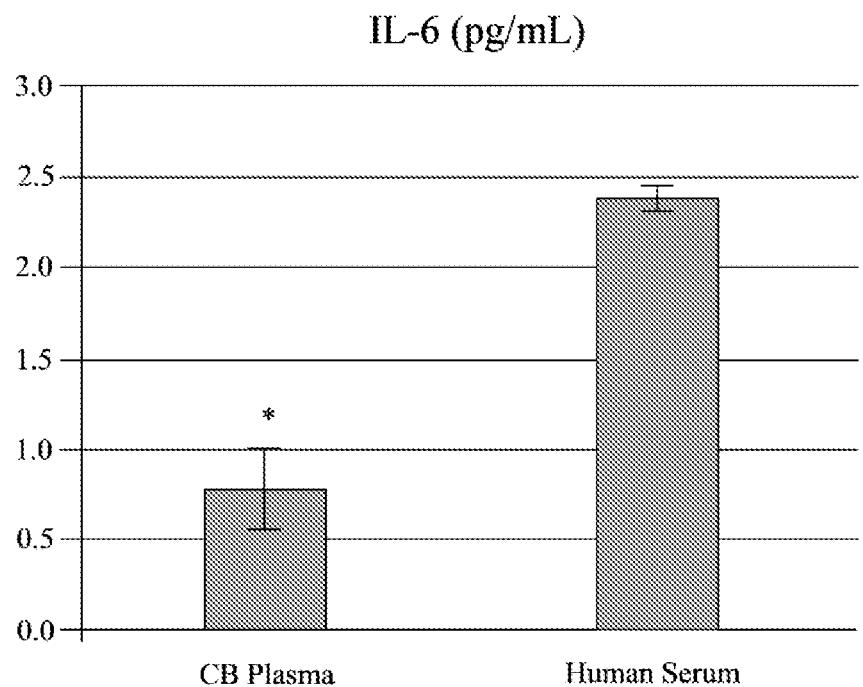
FIG. 1(C) is a graph showing the cytokine profile was assayed on plasma derived from human umbilical cord blood and human adult serum using an ultrasensitive human cytokine panel for IL-6. Results are plotted as mean±SEM. Statistical significance was determined using two tailed t-tests (* p<0.001).
Figure 1D:
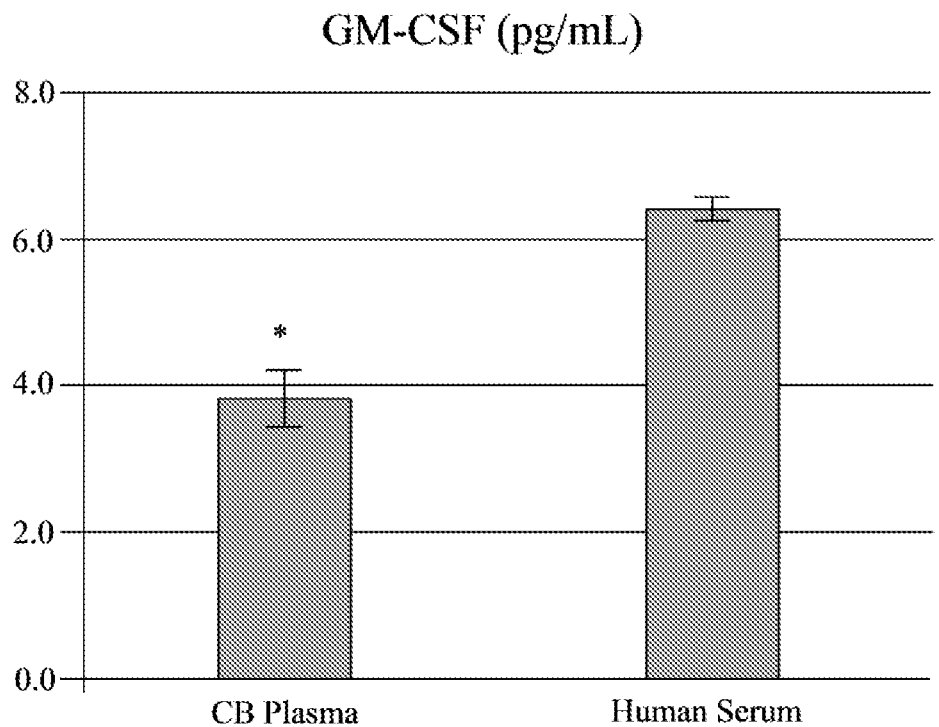
FIG. 1(D) is a graph showing the cytokine profile was assayed on plasma derived from human umbilical cord blood and human adult serum using an ultrasensitive human cytokine panel GM-CSF. Results are plotted as mean±SEM. Statistical significance was determined using two tailed t-tests (* p<0.001).
Figure 1E:
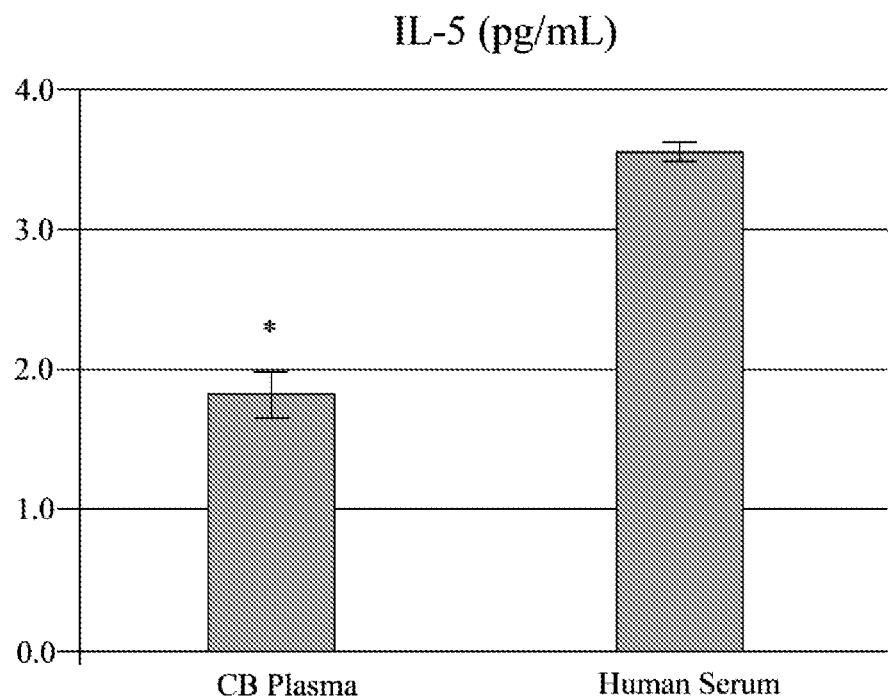
FIG. 1(E) is a graph showing the cytokine profile was assayed on plasma derived from human umbilical cord blood and human adult serum using an ultrasensitive human cytokine panel for IL-5. Results are plotted as mean±SEM. Statistical significance was determined using two tailed t-tests (* p<0.001).
Figure 1F:
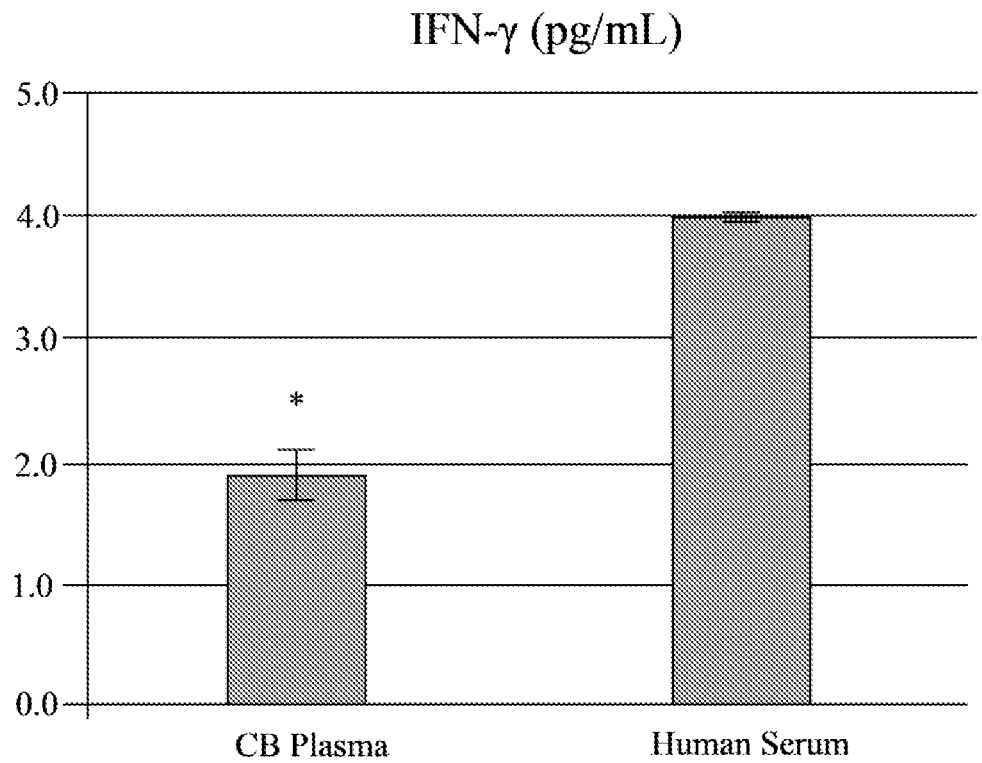
FIG. 1(F) is a graph showing the cytokine profile was assayed on plasma derived from human umbilical cord blood and human adult serum using an ultrasensitive human cytokine panel for IFN-γ. Results are plotted as mean±SEM. Statistical significance was determined using two tailed t-tests (* p<0.001).
Figure 1G:
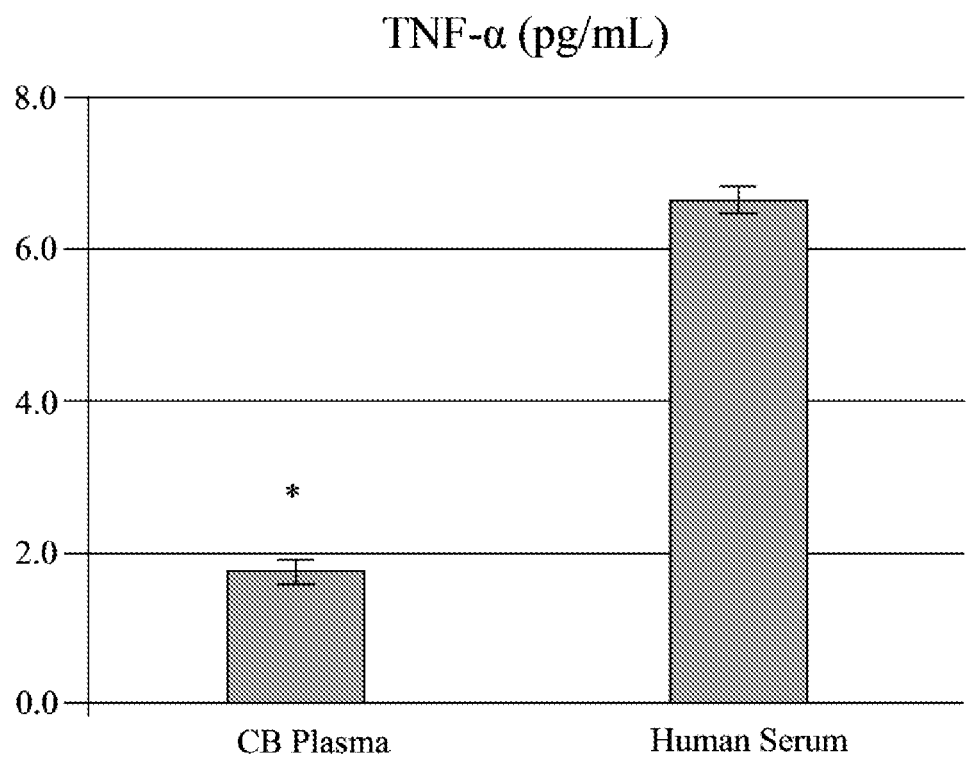
FIG. 1(G) is a graph showing the cytokine profile was assayed on plasma derived from human umbilical cord blood and human adult serum using an ultrasensitive human cytokine panel for TNF-α. Results are plotted as mean±SEM. Statistical significance was determined using two tailed t-tests (* p<0.001).
Figure 1H:
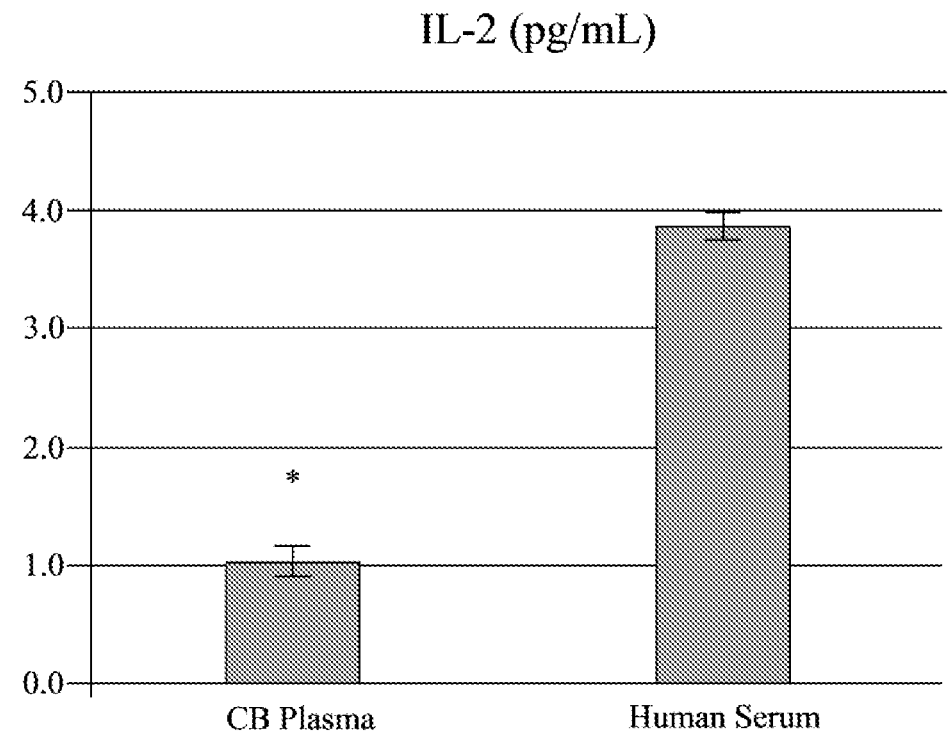
FIG. 1(H) is a graph showing the cytokine profile was assayed on plasma derived from human umbilical cord blood and human adult serum using an ultrasensitive human cytokine panel fir IL-2. Results are plotted as mean±SEM. Statistical significance was determined using two tailed t-tests (* p<0.001).
Figure 1I:
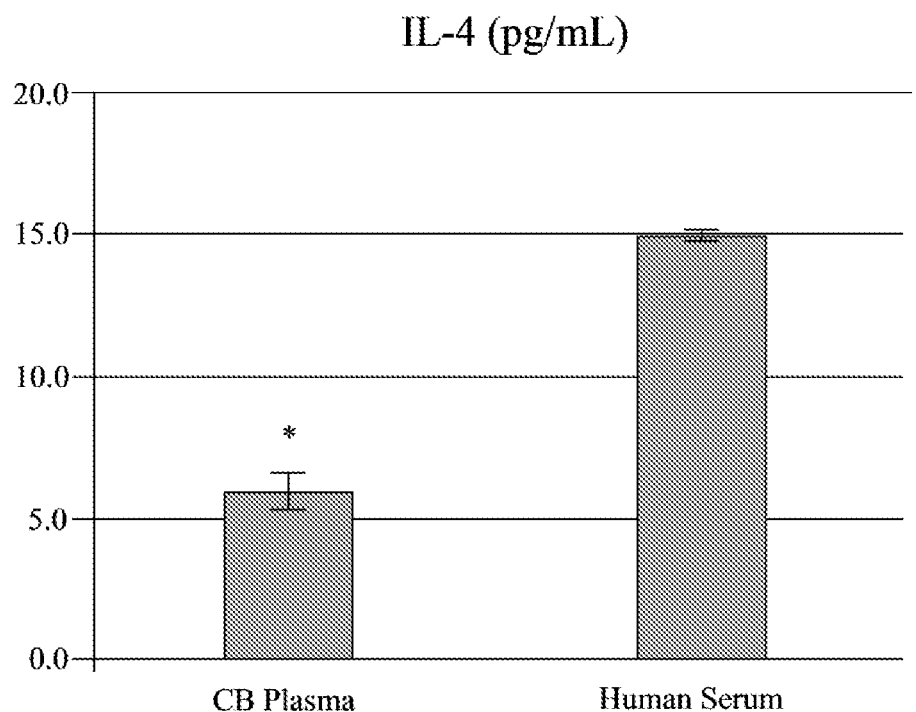
FIG. 1(I) is a graph showing the cytokine profile was assayed on plasma derived from human umbilical cord blood and human adult serum using an ultrasensitive human cytokine panel for IL-4. Results are plotted as mean±SEM. Statistical significance was determined using two tailed t-tests (* p<0.001).

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supercedes any disclosure of an incorporated publication to the extent there is a contradiction.

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

As used herein, "about" means approximately or nearly and in the context of a numerical value or range set forth means ±15% of the numerical.

As used herein, "treat", "treatment", "treating", and the like refer to acting upon a condition, such as autoimmune disease or immunotolerance, with an agent depending on the desired effect, to affect the condition by improving or altering it. The improvement or alteration may include an improvement in symptoms or an alteration in the physiologic pathways associated with the condition. "Treatment," as used herein, covers one or more treatments of a condition in a host (e.g., a mammal, typically a human or non-human animal of veterinary interest), and includes: (a) reducing the risk of occurrence of the condition in a subject determined to be predisposed to the condition but not yet diagnosed, (b) impeding the development of the condition, and/or (c) relieving the condition, e.g., causing regression of the condition and/or relieving one or more condition symptoms (e.g., reduce inflammation).

As used herein, the terms "prophylactically treat" or "prophylactically treating" refers completely or partially preventing (e.g., about 50% or more, about 60% or more, about 70% or more, about 80% or more, about 90% or more, about 95% or more, or about 99% or more) a condition or symptom thereof and/or may be therapeutic in terms of a partial or complete cure or alleviation for a condition and/or adverse effect attributable to the condition.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one or more such excipients, diluents, carriers, and adjuvants.

The term "therapeutically effective amount" as used herein describes concentrations or amounts of components such as stem cells, plasma or other agents which are effective for producing an intended result, including preventing further neurodegenerative disease, or treating a neurodegenerative disease, such as ischemia, amyotrophic lateral sclerosis, Alzheimer's disease, traumatic brain injury, Parkinson's disease or multiple sclerosis. Compositions according to the present invention may be used to effect a favorable change on immune or neuronal cells, whether that change is an improvement, such as stopping or reversing the disease, or relieving to some extent one or more of the symptoms of the condition being treated, and/or that amount that will prevent, to some extent, one or more of the symptoms of the condition that the host being treated has or is at risk of developing, or a complete cure of the disease or condition treated.

The term "administration" refers to introducing an agent of the present disclosure into a patient. One preferred route of administration of the agent is oral administration. Another preferred route is intravenous administration. However, any route of administration, such as parenteral, topical, subcutaneous, peritoneal, intraarterial, inhalation, vaginal, rectal, nasal, introduction into the cerebrospinal fluid, or instillation into body compartments can be used.

As used herein, the term "subject," "patient," or "organism" includes humans and mammals (e.g., mice, rats, pigs, cats, dogs, and horses). Typical patients to which an agent(s) of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like.

The term "umbilical cord blood" is used herein to refer to blood obtained from a neonate or fetus, most preferably a neonate and preferably refers to blood that is obtained from the umbilical cord or the placenta of newborns. Preferably, the umbilical cord blood is isolated from a human newborn. The use of umbilical cord blood as a source of mononuclear cells is advantageous because it can be obtained relatively easily and without trauma to the donor. Umbilical cord blood cells can be used for autologous transplantation or allogenic transplantation, when and if needed. Umbilical cord blood is preferably obtained by direct drainage from the cord an/or by needle aspiration from the delivered placenta at the root and at distended veins. As used herein, the term "cells obtained from umbilical cord blood" refers to cells that are present within umbilical cord blood. In one embodiment, the cells obtained from umbilical cord blood are mononucleated cells that are further isolated from the umbilical cord blood.

Example 1

The human umbilical cord blood plasma (hUCBP) was obtained during isolation of the MNC hUCB (Saneron CCEL Therapeutics Inc.; n=4; 1 male: 3 female). The blood was collected in sterile tubes with heparin (10 units of heparin per 1 mL of blood; BD, Franklin Lakes, NJ, USA) at the time of birth using venipuncture of the umbilical vein. The UCB was diluted (1:1) with sterile phosphate buffered saline (PBS) without $Mg^{2+}$ and $Ca^{2+}$ (Sigma-Aldrich, St. Louis, MO, USA) at 37° C., and overlaid on 12.5 mL of Ficoll (Ficoll-Paque™ Premium 1.077, GE Healthcare, Cat No. 17-5442-02) in 50 mL sterile centrifuge tubes (BD Falcon, Cat No. 352074, Bedford, MA, USA). The blood samples were centrifuged at 400×g for 40 min at 26° C. and the mononuclear cell (MNC) layer was transferred with plasma to new 50 mL tubes by using 10 mL serological pipettes (Fisher brand, Cat No. 13-678-11E, Waltham, MA, USA). The MNCs with plasma were centrifuged at 440×g for 30 min at 21° C. and the plasma collected from the tube. Plasma was stored at −20° C. The MNCs were washed twice in 30 mL of PBS at 440×g for 13 min at 21° C. The cell numbers and viability were determined using a Vi-CELL Viability Analyzer (Beckman Coulter, Brea, CA, USA). The MNCs were frozen in Cryopreservation Media (Saneron CCEL Therapeutics, Inc. Tampa, FL, USA) at $2\times10^6$ cells per vial and stored in liquid nitrogen.

Data are presented as mean±S.E.M. The results were evaluated using ANOVA and Tukey's post hoc test or a paired Student's t-test (Excel; Microsoft, Redmond, WA, USA). A p value <0.05 was considered significant.

A cytokine profile was performed on the cord blood plasma compared to commercially available adult human serum (Atlanta Biologicals, Cat. No. 540110).

Figure 1J:
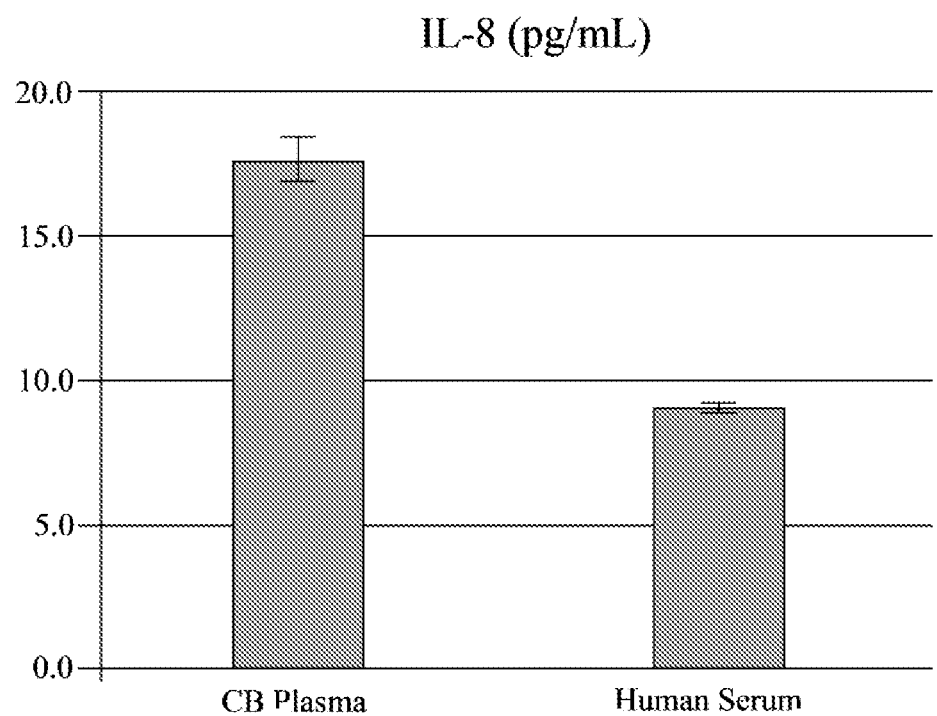
FIG. 1(J) is a graph showing the cytokine profile was assayed on plasma derived from human umbilical cord blood and human adult serum using an ultrasensitive human cytokine panel for IL-8. Results are plotted as mean±SEM. Statistical significance was determined using two tailed t-tests (* p<0.001).

Cord blood plasma was found to possess higher levels of the pro- and immunomodulatory cytokines IL-1β and IL-8 compared to adult blood serum, as seen in FIG. 1(A) and FIG. 1(J). However, the cord blood possessed lower levels of IL-10, IL-6, GM-CSF, IL-5, IFN-γ, TNF-α, IL-2, and IL-4 compared to adult blood serum, as seen in FIGS. 1(B), 1(C), 1(D), 1(E), 1(F), 1(G), 1(H), and 1(I). The cytokine levels were significantly different for IL-5, IFN-γ, TNF-α, IL-2, IL-4, GM-CSF, and IL-6, major pro-inflammatory cytokines. This evidences the anti-inflammatory and immuno-modulatory properties of cord blood plasma. As such, cord blood plasma is a useful therapeutic agent, and can alternatively be used as a diluent in cell administration in order to provide a beneficial environment for the transplanted cells.

Example 2

A total of twelve ALS patients (11 males and 1 female, mean age 53±2.7 years; range 39-69), with a confirmed diagnosis of "Definite ALS" by a Board-certified neurologist (primary neurologist), and six healthy volunteers (3 males and 3 females, mean age 61.3±4.8 years; range 38-69) were enrolled in the study, as seen in the Table. Eleven patients were Caucasian, and one patient was African-American. The healthy volunteers were gender- and age-matched to ALS patients and had no neurological, autoimmune, systemic, or psychiatric diseases. Each participant signed an Informed Consent Form prior to enrolling in the study. The Patient Care Database Form and Medical History Form were completed by each patient and healthy volunteer. A neurological exam was performed upon each study participant. Each study participant was graded on the ALS Functional Rating Scale (ALSFRS; maximum score 40) and ALSFRS-revised (ALSFRS-R; including pulmonary/respiratory function; maximum score 48) using the on-line ALS C.A.R.E. Program (Center for Outcomes Research, Univ. Massachusetts Medical School, Worcester, MA) from data collected by the same neurologist.

The ALS patients were divided into three groups based on their ALSFRS assessment scores with four patients in each; Group 1 (late stage; ALSFRS <20; 17.75±0.9), Group 2 (intermediate; 20<ALSFRS<30; 22±0.7), and Group 3 (early stage; ALSFRS score >30; 32.5±1.0). The three groups are significantly different based on ALSFRS and ALSFRS-R scores (p<0.05) but not age, disease duration or time from diagnosis. All healthy control patients scored 40/48 on the ALSFRS/ALSFRS-R assessments.

TABLE 1

ALS patient demographics.

| | All ALS patients | Patients grouped by ALSFRS Score | | | Healthy volunteers |
|---|---|---|---|---|---|
| n | 12 | Group 1<br>4 | Group 2<br>4 | Group 3<br>4 | 6 |
| Age (years) mean ± SEM | 53 ± 2.7 (39-69) | 51.3 ± 6.4 (39-69) | 54.0 ± 5.2 (39-63) | 53.8 ± 3.1 (45-59) | 61.3 ± 4.8 (38-69) |
| Sex (male/female) | 11/1 | 4/0 | 3/1 | 4/0 | 3/3 |
| ALSFRS mean ± SEM | 24.1 ± 1.9 (15-35) | 17.8 ± 0.9 (15-19) | 22 ± 0.7 (21-24) | 32.5 ± 1.0 (30-35) | 40.0 ± 0.0 |
| ALSFRS-R mean ± SEM | 30.7 ± 2.1 (21-41) | 24 ± 1.5 (21-27) | 28.5 ± 1.6 (25-32) | 39.5 ± 1.0 (37-41) | 48.0 ± 0.0 |
| Disease onset (months) mean ± SEM | 42.5 ± 7.8 (11-96) | 53.5 ± 13.9 (26-88) | 47 ± 16.8 (20-96) | 27 ± 8.4 (11-49) | NA |
| Months since diagnosis mean ± SEM | 21.5 ± 4.6 (5-53) | 26 ± 6.9 (13-43) | 25.8 ± 9.9 (7-53) | 12.8 ± 7.1 (5-34) | NA |

Peripheral blood (~80 mL) from ALS patients and healthy volunteers was obtained via venipuncture by a nurse. Hematological analysis (complete blood cell [CBC] and white blood cell differential [WBCD] counts) was performed for each blood sample (performed by Quest Diagnostics, Inc., Madison, NJ). Data are presented as mean±S.E.M. The results were evaluated using ANOVA and Tukey's post hoc test or a paired Student's t-test (Excel; Microsoft, Redmond, WA, USA). A p value <0.05 was considered significant.

Figure 2:
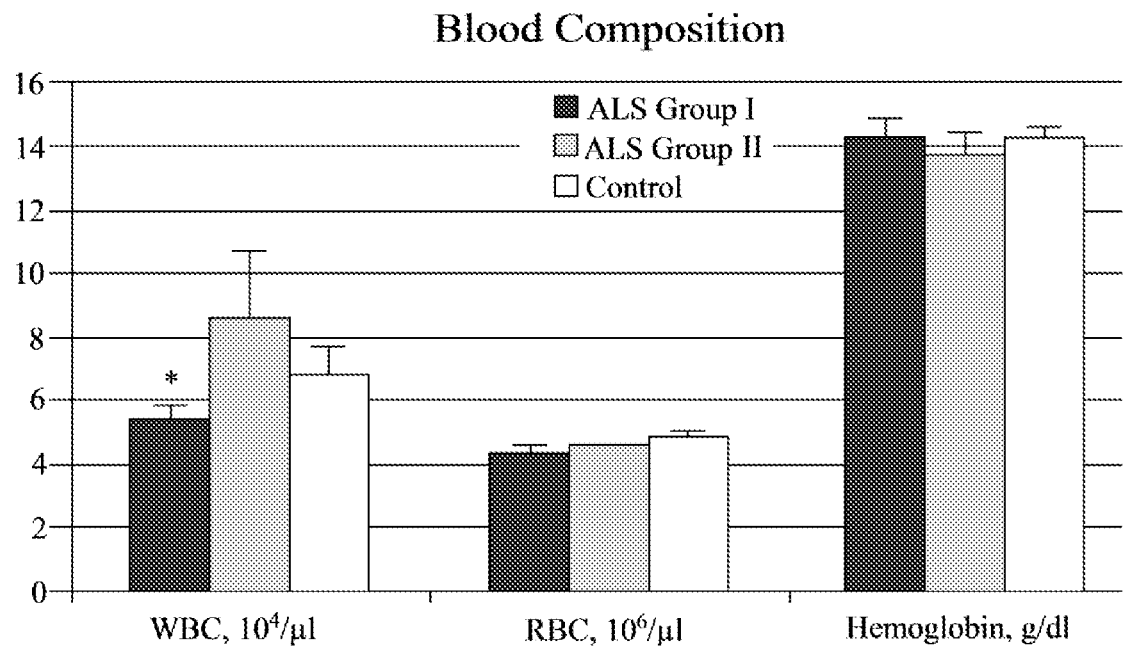
FIG. 2 is a graph showing hematological analysis of the peripheral blood. Seven ALS patients (Group I) had significantly (p=0.0278) low normal WBC counts and two ALS patients (Group II) had higher counts than healthy volunteers. Although, there were no significant differences in RBC counts or hemoglobin level between ALS patients and healthy volunteers, two patients from Group I had low normal RBC ($3.9 \times 10^6/\mu L$ and $3.6 \times 10^6/\mu L$) and hemoglobin level (12.4 g/dL and 12.1 g/dL) compared to reference range for RBC ($4.2$-$5.8 \times 10^6/\mu L$) and hemoglobin (13.2-17.1 g/dL). Significantly fewer lymphocytes (p=0.0255) and elevated neutrophils (p=0.0218) were noted in Group II compared to both Group I and healthy volunteers.
Figure 3:
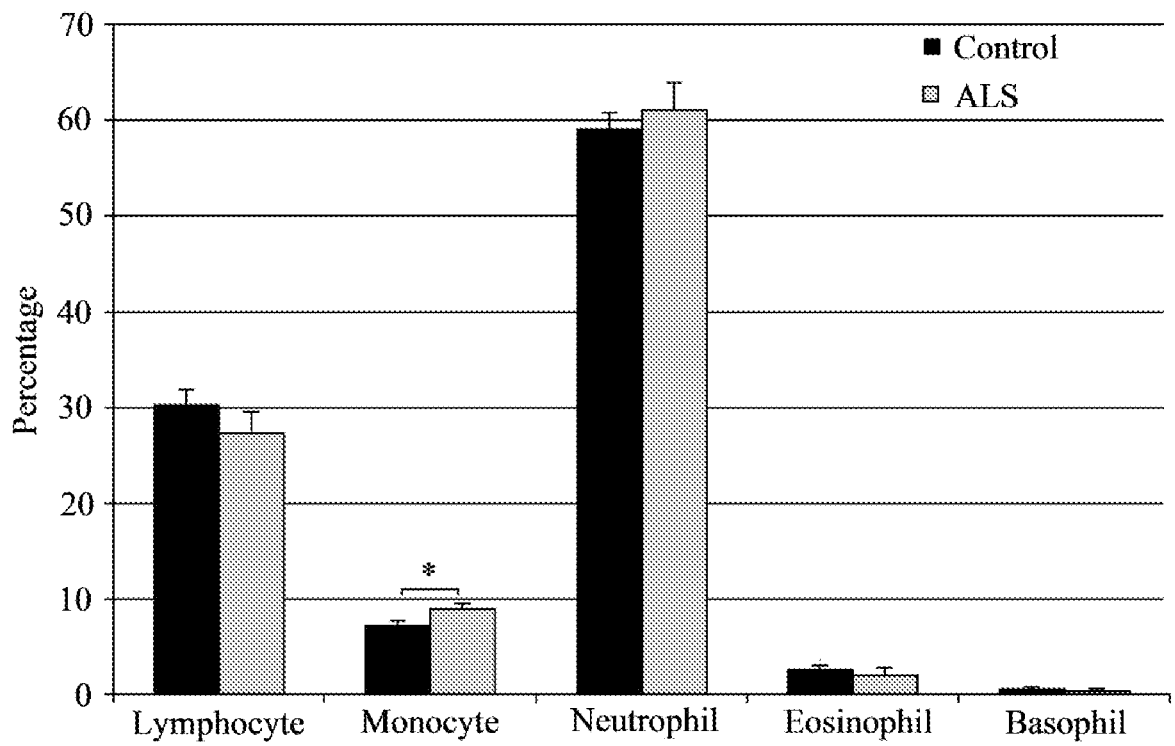
FIG. 3 shows hematological analysis of the peripheral blood. No significant differences in the hematological analysis of the peripheral blood were observed between Amyotrophic lateral sclerosis (ALS) patients (n=10) and healthy volunteers (n=5), except for a significant increase in monocyte number (*p<0.05).

Seven ALS patients (Group I) had significantly (p=0.0278) low normal WBC counts and two ALS patients (Group II) had higher counts than healthy volunteers. Although, there were no significant differences in RBC counts or hemoglobin level between ALS patients and healthy volunteers, two patients from Group I had low normal RBC ($3.9\times10^6/\mu L$ and $3.6\times10^6/\mu L$) and hemoglobin level (12.4 g/dL and 12.1 g/dL) compared to reference range for RBC ($4.2\text{-}5.8\times10^6/\mu L$) and hemoglobin (13.2-17.1 g/dL). However, in general Group I ALS patients exhibited lower WBC compared to controls, whereas Group II ALS patients exhibited higher WBC counts, as seen in FIG. 2. An analysis of the WBC constituents showed control patient blood contains slightly higher lymphocyte cells and eosinophils, whereas ALS patient possess slightly higher neutrophil counts, and higher monocyte cell counts, as seen in FIG. 3. Of the differences seen, only the alterations in monocyte levels were statistically significant, which were significantly higher in all ALS patients (8.98% vs. 7.3%; p<0.05). However, when the ALS patient population was segregated based on ALSFRS, significantly fewer lymphocytes (p=0.0255) and elevated neutrophils (p=0.0218) were noted in Group II compared to both Group I and healthy volunteers.

Figure 4:
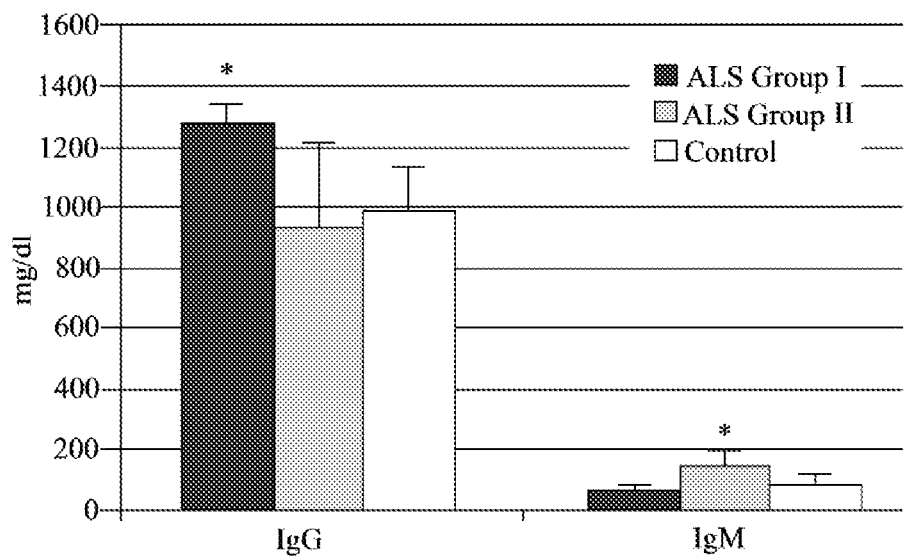
FIG. 4 is a graph showing immunological analysis of the peripheral blood. Levels of IgG were significantly higher in Group I compared to both healthy volunteers (p=0.0364) and Group II (p=0.0511), while the IgM profile was opposite, with significant (p=0.0357) elevation in Group II. Note: Reference ranges for adults: IgG is 654-1618 mg/dL; IgM is 48-271 mg/dL. Reference ranges for cord blood: IgG is 553-1360 mg/dL; IgM is <17 mg/dL

Levels of IgG were significantly higher in Group I compared to both healthy volunteers (p=0.0364) and Group II (p=0.0511), while the IgM profile was opposite, with significant (p=0.0357) elevation in Group II, seen in FIG. 4. By comparison, typically ranges for IgG in healthy adults is 654-1618 mg/dL, and for IgM is 48-271 mg/dL. Additionally, the reference ranges for IgG in cord blood is 553-1360 mg/dL, and for IgM is <17 mg/dL.

Blood smears from each blood sample were fixed in methanol for immunocytochemical analysis of CD4 and CD8 cells. Briefly, the mouse monoclonal antibodies CD4 (ab848) or CD8 (ab17147) (1:200, Abcam PLC, Cambridge, UK) were applied on a slide after 60 min pre-incubation with 10% normal goat serum and Triton X100 in phosphate buffered saline (PBS). After incubating overnight at 4° C., the slides were washed and incubated with goat anti-mouse secondary antibody conjugated to rhodamine (1:1200, Alexa, Molecular Probes) or FITC (1:500, Alexa, Molecular Probes) for 2 hrs at room temperature. Then the slides were rinsed in PBS and coverslipped with Vectashield (DAPI, Vector) and examined under epifluorescence. Counts of CD4 and CD8 positive cells were performed on five representative images from each slide using ImagePro Software. The percentages of CD4 and CD8 positive cells were calculated based upon the total number of DAPI positive cells. Also, routine Giemsa staining was performed for each blood sample.

Figure 5A:
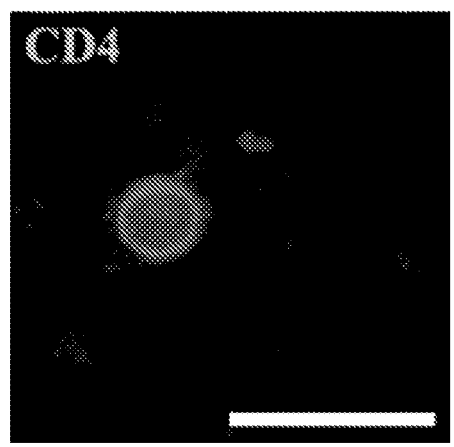
FIG. 5(A) is a microscopic image showing immunocytochemical analysis of CD4. Scale bar in images is 25 μm.
Figure 5B:
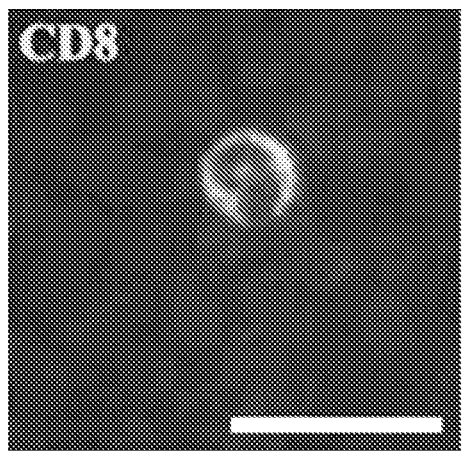
FIG. 5(B) is a microscopic image showing immunocytochemical analysis of CD8. Scale bar in images is 25 μm.

The ratio of CD4 staining, compared to CD8 staining was analyzed. In Group I ALS patients, the ratio of CD4/CD8 was similar to healthy control blood samples (1.63±0.13 for Group I, 1.59±0.09 for control). However, in Group II ALS patients, the ratio of CD4/CD8 was elevated (1.86±0.11), as seen in FIG. 5.

ALS patients showed hematological and immunological differences depending upon the stage of disease. Patients in Group I, as defined by ALSRS, had significantly lower WBC counts and higher IgG levels than patients in Group II. The Group II patients had significantly higher percentages of neutrophils and lower percentages of lymphocytes in WBC, higher IgM levels, and an elevated CD4/CD8 ratio. These results may indicate early stage infections and/or inflammation in the Group II patients Example 3

Fresh peripheral blood from ALS patients and healthy volunteers was collected in sterile tubes with heparin (10 units of heparin per 1 mL of blood; BD, Franklin Lakes, NJ, USA) and diluted (1:1) with sterile phosphate buffered saline (PBS) without $Mg^{2+}$ and $Ca^{2+}$ (Sigma-Aldrich, St. Louis, MO, USA) at 37° C. Then, 12.5 mL of Ficoll (Histopaque-1077, Sigma-Aldrich, Cat No. 10771) was added into 50 mL sterile centrifuge tubes (BD Falcon, Cat No. 352074, Bedford, MA, USA). Blood samples diluted in PBS were overlaid on the Ficoll and centrifuged at 400×g for 40 min at 26° C. The MNC layer was transferred with plasma to new 50 mL tubes by using 10 mL serological pipettes (Fisherbrand, Cat No. 13-678-11E, Waltham, MA, USA). The MNCs were washed twice in 30 mL of PBS at 440×g for 13 min at 21° C. The cell numbers and viability were determined using a Vi-CELL Viability Analyzer (Beckman Coulter, Brea, CA, USA). The MNCs were frozen in Cryopreservation Media (Saneron CCEL Therapeutics, Inc. Tampa, FL, USA) at $2\times10^6$ cells per vial and stored in liquid nitrogen. Cell samples contained approximately 7.4 million white blood cells per millimeter, 11.6% granulocytes, and 1-4% $CD34^+$ cells.

Cryopreserved MNCs were thawed rapidly at 37° C. then transferred slowly with a pipette into a 15-ml centrifuge tube containing sterile PBS. The cells were centrifuged (400×g/7 min), the supernatant discarded, and the process repeated. After the final wash, viability of cells was assessed using the 0.4% trypan blue dye exclusion method prior to culture. The cells ($25\times10^3$) were plated in triplicate in 96-well plates (Fisher Brand) with Roswell Park Memorial Institute (RPMI)-1640/10% fetal bovine serum (FBS) (Medium 1; all from Sigma-Aldrich). After 24 hours incubation, phytohemagglutinin (PHA; Sigma-Aldrich) was added to the culture at 1 μg/mL or 10 μg/mL. The cell colonies in the entire well were counted at 24, 48, and 72 hours incubation. The index of stimulation (IS) was determined as the number of induced colonies/number spontaneous colonies in the control wells.

Data are presented as mean±S.E.M. The results were evaluated using ANOVA and Tukey's post hoc test or a paired Student's t-test (Excel; Microsoft, Redmond, WA, USA). A p value <0.05 was considered significant.

Figure 6:
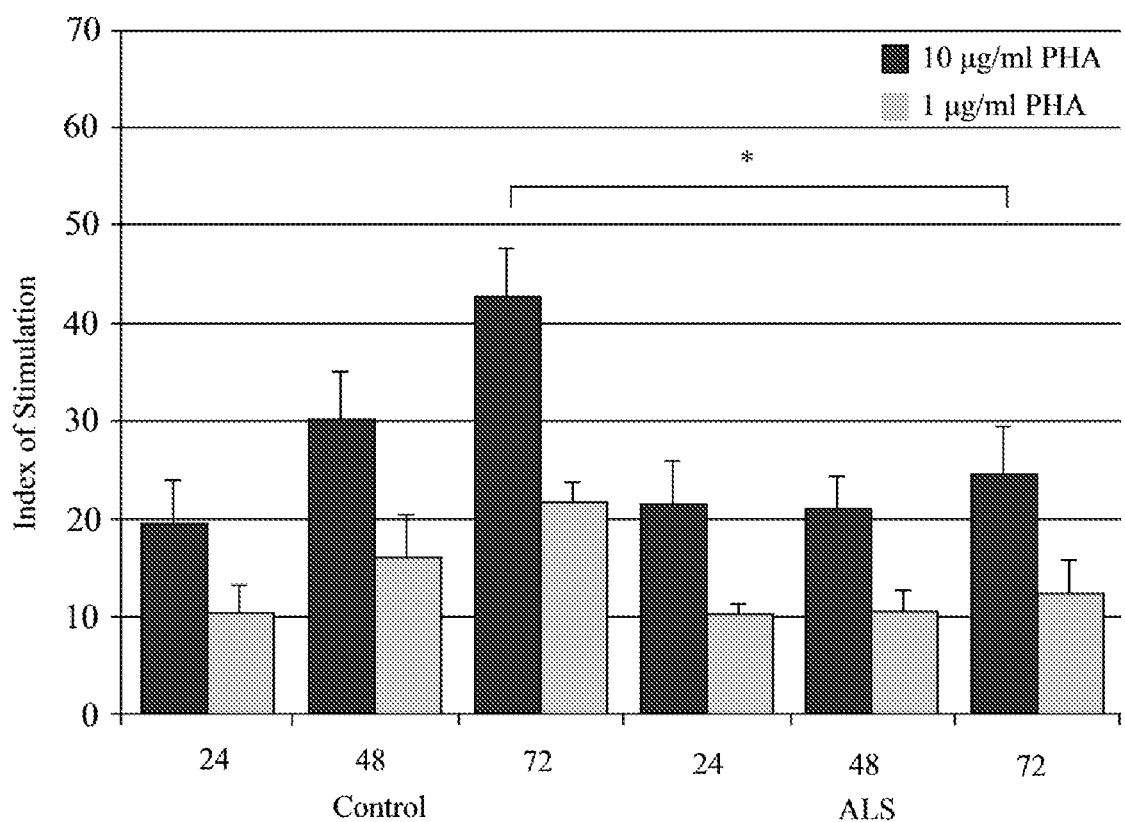
FIG. 6 is a graph showing PHA-induced proliferation of MNCs isolated from peripheral blood in Medium 1 (containing FBS) and Medium 2 (containing hUCBP). The response profile of mononuclear cells (MNCs) from healthy controls (n=5) to phytohemagglutinin (PHA; 10 μg/mL) stimulation when the cells were incubated with Medium 1 (fetal bovine serum [FBS] only containing) showed a normal increasing index of stimulation (IS) with time. However, in ALS patients (n=12), this was not observed. A smaller, but similar effect was seen with the lower dose (1 μg/mL). The 10 μg/mL PHA IS was significantly higher than the 1 μg/mL at all time points for both ALS and controls (p<0.05) and the 72 hr 10 μg/mL was significantly higher in controls.

The peripheral blood isolated MNCs were cultured in vitro with the mitogen PHA, seen in FIG. 6. There were three different response profiles of MNCs to PHA (10 μg/mL) stimulation when the cells were incubated with Medium 1. In healthy control volunteers, the index of stimulation was 32 at 24 h to 50 at 72 h of incubation and showed apparent linear increases over time. MNCs from some ALS patients was similar, but abnormal extensive proliferation (increased stimulation with a decreasing trend over time) and non-inducible proliferation were observed, from a value of 10 at 24 hours post-treatment to a value of 20 at 72 hours post-treatment for the lower treatment dose (1 μg/mL PHA). Higher dosages (10 μg/mL PHA) display a similar relationship, with values ranging from 20 at 24 hours post-treatment to 40 at 72 hours post-treatment. These trends display a typical time- and dose-dependent increase in response to PHA stimulation (p<0.05; n=5). Dose-dependent effects were seen in ALS patients, as the high-dose PHA stimulation consistently increased the index of stimulation (p<0.05), but no time-dependent increases were observed. At 72 hrs and a dose of 10 μg/ml, the control patients' IS was significantly higher than that for the ALS MNCs. Interestingly, low response to PHA at 1 μg/mL concentration was found in all ALS patients compared to control healthy volunteers.

Figure 7:
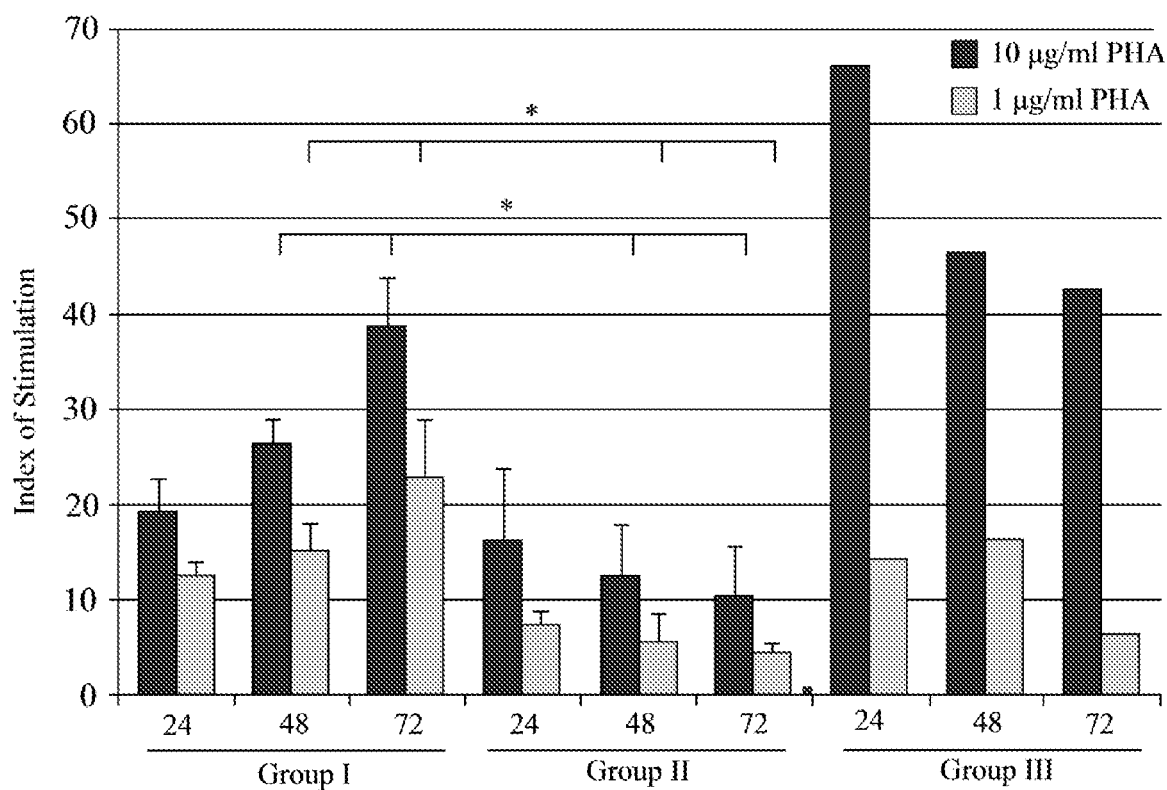
FIG. 7 is a graph showing PHA-induced proliferation of MNCs isolated from peripheral blood in Medium 1 (containing FBS) and Medium 2 (containing hUCBP). Examination of the responses to PHA stimulation revealed that there were three different response profiles for the ALS patients' cells. The IS of MNCs from some ALS patients was similar (Group I; n=5), but abnormal extensive proliferation (increased stimulation with a decreasing trend over time; Group III; n=1) and non-inducible proliferation were also observed (Group II). Group II (n=6) was significantly different from both Group I and controls at both concentrations (* p<0.05) and the 10 μg/mL PHA IS was significantly higher than the 1 μg/mL at all time points for Group II ALS and control only (p<0.05).

Further analysis of the ALS data revealed three distinct profiles that emerged when the isolated MNCs were incubated with PHA, seen in FIG. 7. The index of stimulation (IS) for some ALS patients was similar to that of controls showing the typical time- and dose-dependent response without significant difference (Group I; n=5). However, abnormal extensive proliferation (an increased stimulation with a decreasing trend over time) was observed in one patient (Group III; this is neither the female patient, the African-American, nor the patient with the lowest ALS score, though it is the oldest patient). Non-inducible proliferation was observed with MNCs isolated from other ALS patients (Group II; n=6). Group II showed a significant dose-dependent response at each time point (p<0.05) and was significantly reduced compared to Group I and controls at 48 and 72 hrs for both concentrations of PHA. Additionally, MNCs isolated from human umbilical cord blood (hUCB) showed little to no cell proliferation with either concentration of PHA used (data not shown). The normal, abnormal extensive proliferation and non-responding patients did not correlate with the three ALSFRS-designated groups. Re-analysis of the previous parameters using this grouping also did not reveal any significant differences. Since Group III only contained one patient, no statistics could be performed using this group.

ALS patients differed in lymphocyte functionality, possible due to differences in immune response. Patients with abnormally extensive cell proliferation (Group III) in response to mitogen (PHA) in vitro probably have autoimmunity impairment while non-inducible proliferation (Group II) may indicate immune deficiency.

Example 4

The hUCB plasma (hUCBP) was obtained during isolation of the MNC hUCB cells, as described previously. The blood was collected in sterile tubes with heparin (10 units of heparin per 1 mL of blood; BD, Franklin Lakes, NJ, USA) at the time of birth using venipuncture of the umbilical vein. The UCB was diluted (1:1) with sterile phosphate buffered saline (PBS) without $Mg^{2+}$ and $Ca^{2+}$ (Sigma-Aldrich, St. Louis, MO, USA) at 37° C., and overlaid on 12.5 mL of Ficoll (Histopaque-1077, Sigma-Aldrich, Cat No. 10771) in 50 mL sterile centrifuge tubes (BD Falcon, Cat No. 352074, Bedford, MA, USA). The blood samples were centrifuged at 400×g for 40 min at 26° C. and the mononuclear cell (MNC) layer was transferred with plasma to new 50 mL tubes by using 10 mL serological pipettes (Fisherbrand, Cat No. 13-678-11E, Waltham, MA, USA). Plasma was stored at −20° C.

Peripheral blood (~80 mL) from was obtained from the ALS patients and healthy volunteer population via venipuncture by a nurse and processed as described in Example 1. Briefly, blood was collected in heparin tubes (BD, Franklin Lakes, NJ, USA) and diluted in PBS without $Mg^{2+}$ and $Ca^{2+}$ (Sigma-Aldrich, St. Louis, MO, USA) at 37° C., followed by Ficoll extraction (Histopaque-1077, Sigma-Aldrich, Cat No. 10771). The MNCs were washed twice in 30 mL of PBS and MNCs were frozen in Cryopreservation Media (Saneron CCEL Therapeutics, Inc. Tampa, FL, USA) at $2\times10^6$ cells per vial and stored in liquid nitrogen.

Cryopreserved MNCs, described in Example 2, were thawed rapidly at 37° C. then transferred slowly with a pipette into a 15-ml centrifuge tube containing sterile PBS. The cells were centrifuged (400×g/7 min), the supernatant discarded, and the process repeated. Cell viability was determined using trypan blue dye and the cells ($25\times10^3$) plated in triplicate in 96-well plates (Fisher Brand) with RPMI-1640/10% fetal bovine serum (FBS) (Medium 1; all from Sigma-Aldrich), or RPMI-1640/10% hUCBP ABO Rh matched (Medium 2). After 24 hours incubation, phytohemagglutinin (PHA; Sigma-Aldrich) was added to the culture at 1 μg/mL or 10 μg/mL. The cell colonies in the entire well were counted at 24, 48, and 72 hours after addition of PHA. The index of stimulation (IS) was determined as the number of induced colonies/number spontaneous colonies in the control wells.

Data are presented as mean±S.E.M. The results were evaluated using ANOVA and Tukey's post hoc test or a paired Student's t-test (Excel; Microsoft, Redmond, WA, USA). A p value <0.05 was considered significant.

Figure 8:
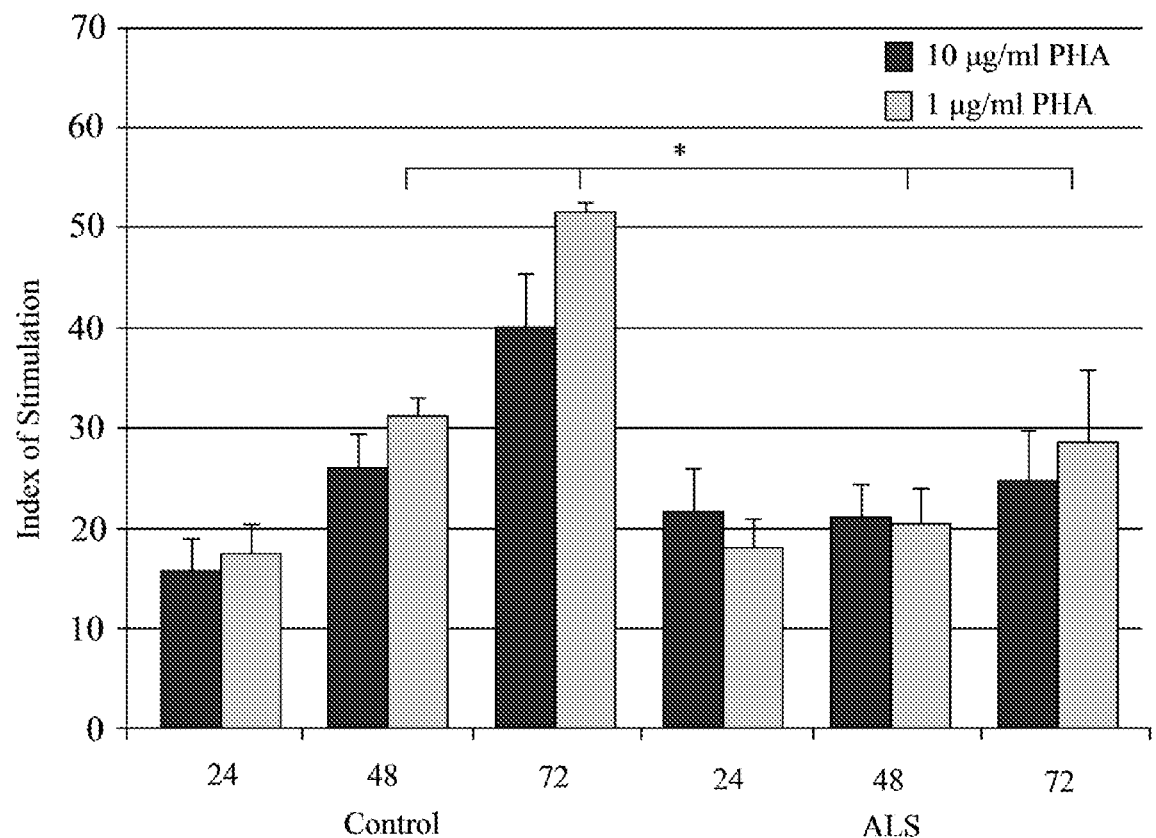
FIG. 8 is a graph showing PHA-induced proliferation of MNCs isolated from peripheral blood in Medium 1 (containing FBS) and Medium 2 (containing hUCBP). When MNCs were cultured in Medium 2 containing hUCB plasma, the proliferation response of cells to PHA (10 μg/mL) of ALS patients remained significantly reduced compared to controls (* p<0.05).
Figure 9A:
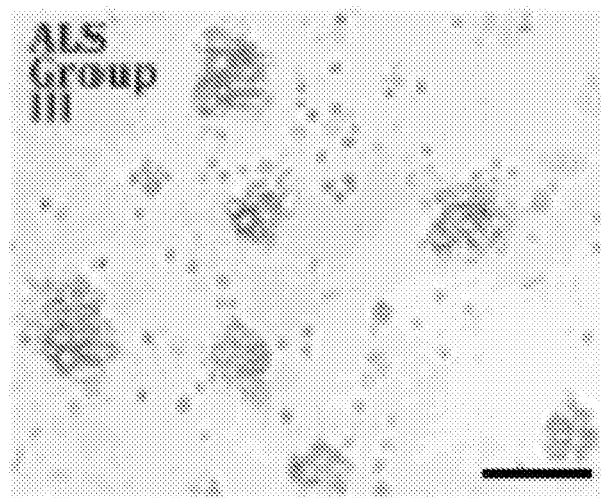
FIG. 9(A) is a microscope image showing PHA-induced proliferation of MNCs isolated from peripheral blood of an ALS patient from Group III, in Medium 1 (containing FBS). Group III; abnormal extensive cell proliferation. Scale bar is 100 μm.
Figure 9B:
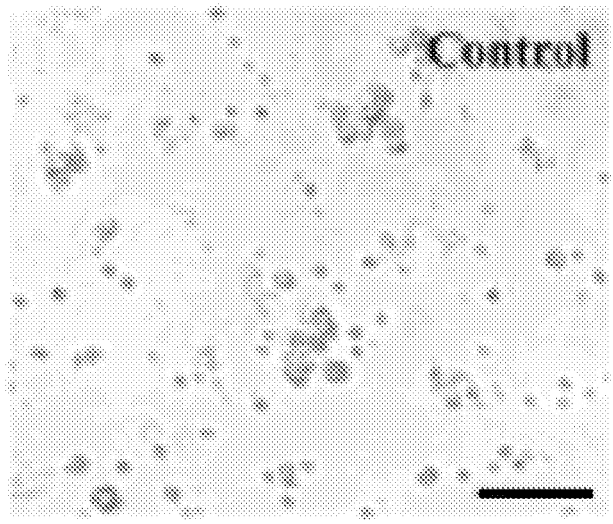
FIG. 9(B) is a microscope image showing PHA-induced proliferation of MNCs isolated from peripheral blood from a healthy control individual, in Medium 1 (containing FBS). Scale bar is 100 μm.
Figure 9C:
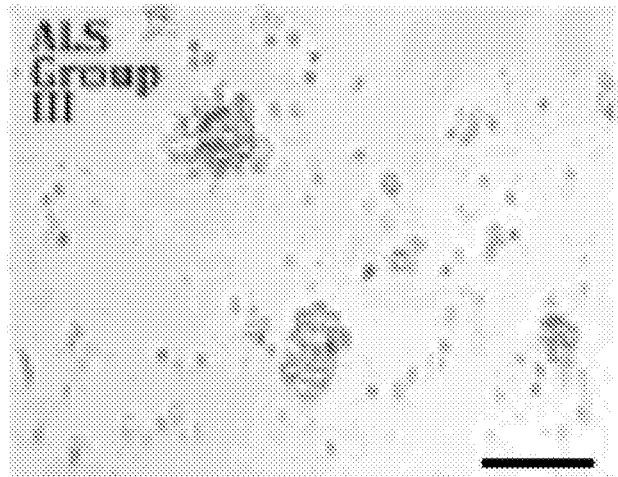
FIG. 9(C) is a microscope image showing PHA-induced proliferation of MNCs isolated from peripheral blood of an ALS patient from Group III, in Medium 2 (containing hUCBP). Images show decreased numbers of colonies in Medium 2 (Group III; abnormal extensive cell proliferation). Scale bar is 100 μm.
Figure 9D:
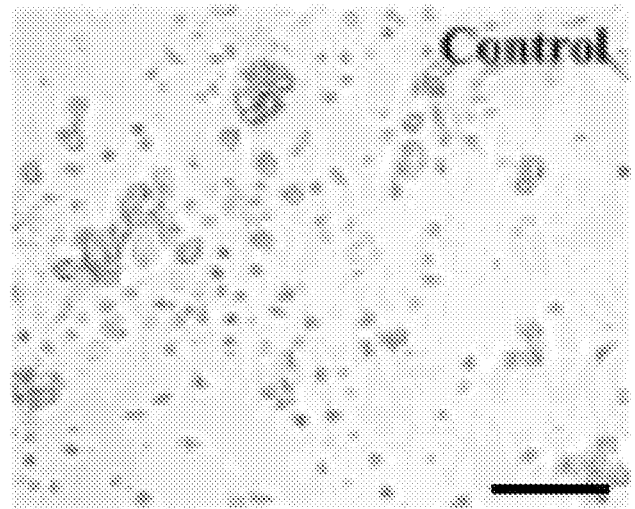
FIG. 9(D) is a microscope image showing PHA-induced proliferation of MNCs isolated from peripheral blood from a healthy control individual, in Medium 2 (containing hUCBP). Images show decreased numbers of colonies in Medium 2. Scale bar is 100 μm.
Figure 10:
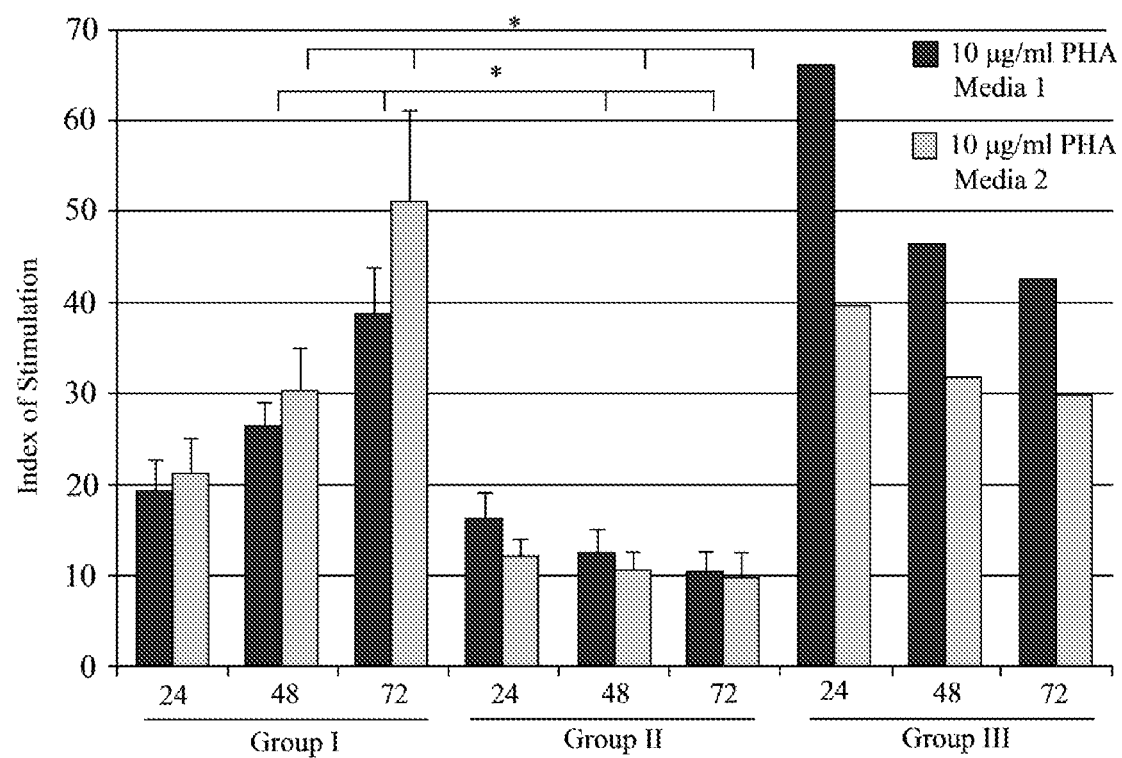
FIG. 10 is a graph showing PHA-induced proliferation of MNCs isolated from peripheral blood in Medium 1 (containing FBS) and Medium 2 (containing hUCBP). Splitting the ALS patients into the previous 3 groups based on their response to PHA in media 1, demonstrated that the proliferation response of cells to PHA (10 μg/mL) was blunted in cells exhibiting abnormal extensive proliferation (Group III) when cultured in Medium 1. An insignificant increase in cell proliferation was observed in cultures with a "normal" response to PHA (Group I) and no significant differences between Media 1 and Media 2 were found in cell cultures with non-inducible proliferation (Group II). Group II remained significantly different from control and Group I with Medium 2 (* p<0.05).

Isolated MNCs cultured with media supplemented with plasma collected from hUCB (Medium 2) and treated with PHA showed a non-significant increase in the IS after incubating on Medium 2 at each point. In the healthy control population, the difference in index of stimulation between media and plasma-supplemented media increased as time progressed, with a difference under 5 at 24 hours and about 10 by 72 hour, as seen in FIG. 8. Cells from all ALS patients appeared to exhibit a mild time-dependent IS response, which was significantly lower than that for the control MNCs at 48 and 72 hrs. However, segregating the ALS population based on PHA response, as undertaken in Example 3, revealed that stimulation of the cells that exhibited abnormal extensive proliferation (Group III) using Medium 1 resulted in clustering of Group III cells, not seen in the control group, as seen in FIG. 9(A) and 9(B). By comparison, the UCB plasma-supplemented medium (Medium 2) showed a blunted expansion, as seen in FIG. 9(C), compared to the control group seen in FIG. 9(D). The modulated stimulation effect seen with Medium 2 was observed at all time points, as seen in FIG. 10. Insignificant increases were observed in cultures with a standard response to PHA (Group I; n=5), while no differences between Medium 1 and Medium 2 were observed from cell cultures that exhibited non-inducible proliferation (Group II). Group II MNCs had a significantly lower index of stimulation than Group I and controls at both 48 and 72 hours with regards to Medium 2. Again, no differences were observed when the patients were grouped by ALSFRS and no correlations were evident.

ALS patients differed in lymphocyte functionality, possibly due to differences in immune response. Patients with abnormally extensive cell proliferation (Group III) in response to mitogen (PHA) in vitro probably have autoimmunity impairment while non-inducible proliferation (Group II) may indicate immune deficiency. Cord blood plasma modulates the cell response to the mitogen (PHA) only in patients with abnormally extensive cell proliferation and was not effective in patients with non-inducible cell proliferation.

These initial results demonstrate that plasma derived from cord blood could be effective in ALS patients with immune dysfunction.

Example 5

Caspase 3/7 activity was determined in MNCs isolated from the peripheral blood of ALS patients to determine the potential of these cells to undergo apoptosis. MNCs isolated from the peripheral blood of ALS patients and healthy volunteers, as described in Example 2. The MNCs were plated and incubated in Medium 1 as described above for 5 days, after which the cells were incubated in Medium 2 for 24 hrs. Caspase 3/7 activities were determined in these cells using a Magic Red Caspase 3/7 kit (Immunochemistry Technologies, LLC, Bloomington, MN, USA). Briefly, 10 μL of the 31X Magic Red-(aspartate-glutamate-valine-aspartate)$^2$, [MR-(DEVD)$^2$] solution was added to each cell well and incubated for 1 hour. Hoechst dye (nuclei staining; Sigma-Aldrich) was added at 1 μL/well and incubated for an additional 5 min. Immediately after incubation, five representative photomicrographs were produced and counts of Caspase 3/7- and Hoechst-positive cells were performed using ImagePro Software. Apoptotic Caspase 3/7 cells were expressed as the percentage of the total Hoechst cells.

Data are presented as mean±S.E.M. The results were evaluated using ANOVA and Tukey's post hoc test or a paired Student's t-test (Excel; Microsoft, Redmond, WA, USA). A p value <0.05 was considered significant.

Figure 11:
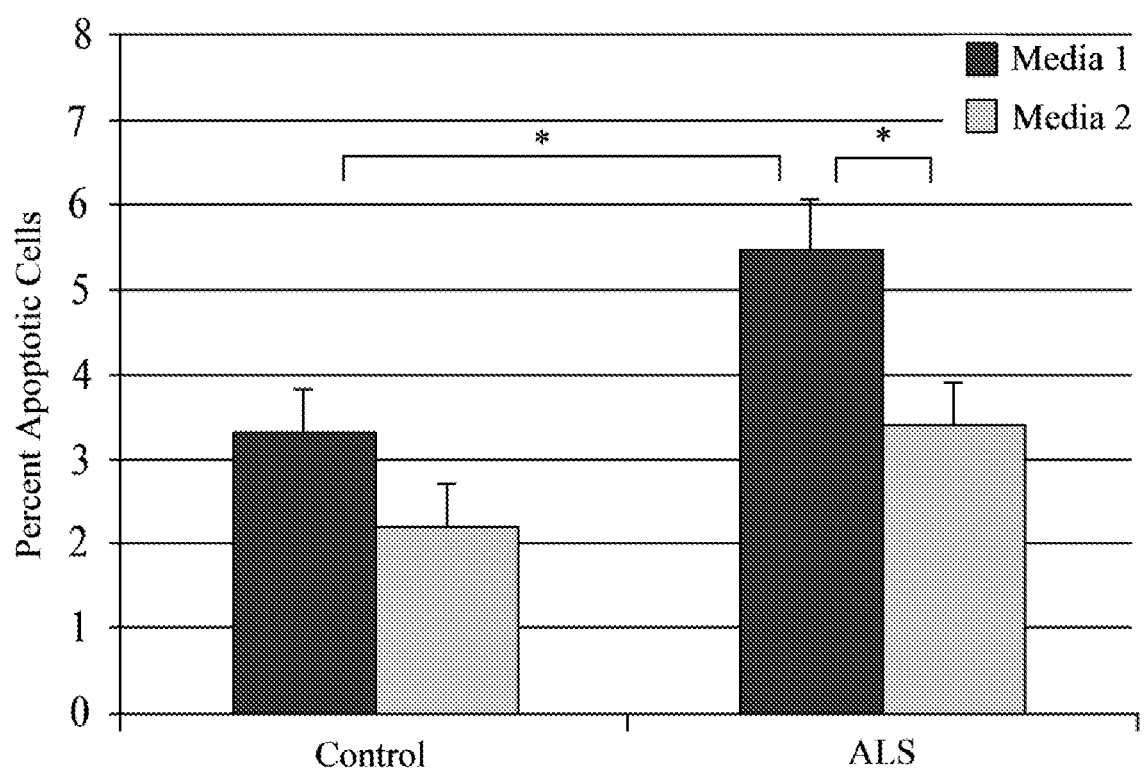
FIG. 11 is a graph showing caspase 3/7 activity in MNCs isolated from the peripheral blood of ALS patients. Many Caspase-3/7-positive cells were found in the MNCs of ALS patients cultured for 5 days in Medium 1, which was significantly different from that in controls (* p<0.05). When Medium 1 was changed to Medium 2 containing hUCB plasma for 24 hrs, the apoptotic activity of cells in the ALS patients was significantly lower than ion medium 1 (p<0.05).
Figure 12:
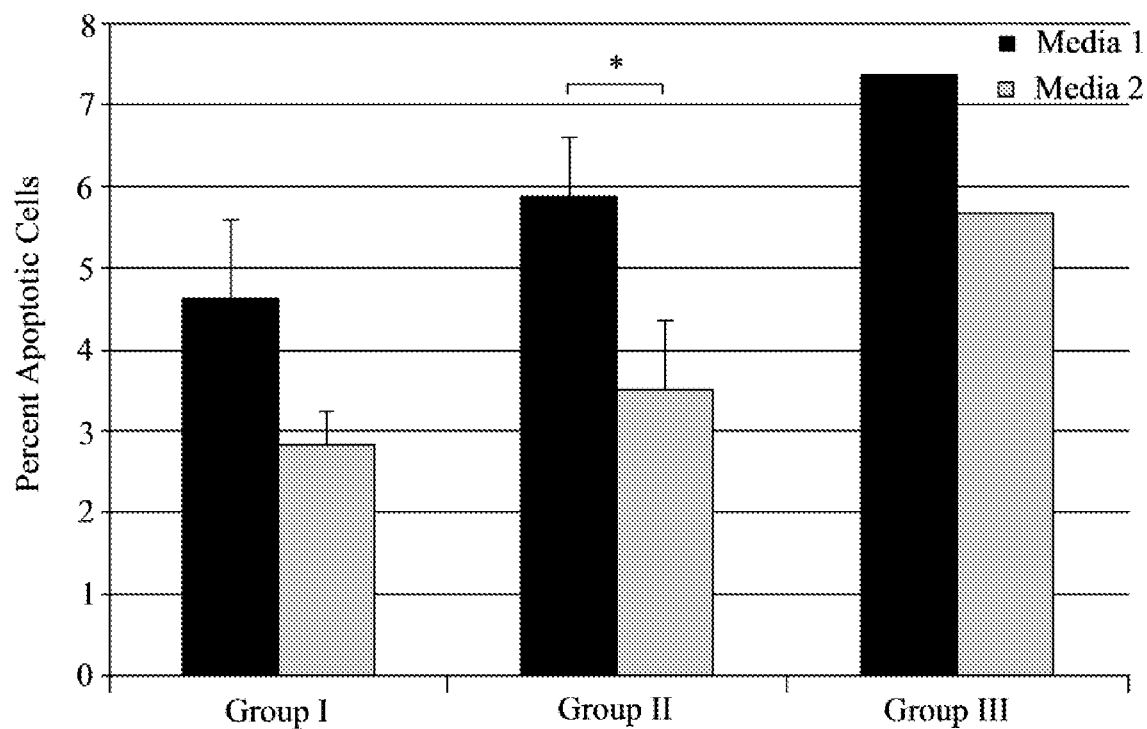
FIG. 12 is a graph showing caspase 3/7 activity in MNCs isolated from the peripheral blood of ALS patients. More Caspase-3/7-positive cells were found in patients with abnormal extensive proliferation (Group III) and non-inducible proliferation (Group II) compared to patients with "normal" response to PHA (Group I), though this was not significant. Cultured MNCs in Medium 2 showed significantly decreased apoptotic activity in patients with an abnormal response to PHA stimulation (p<0.05).
Figure 13A:
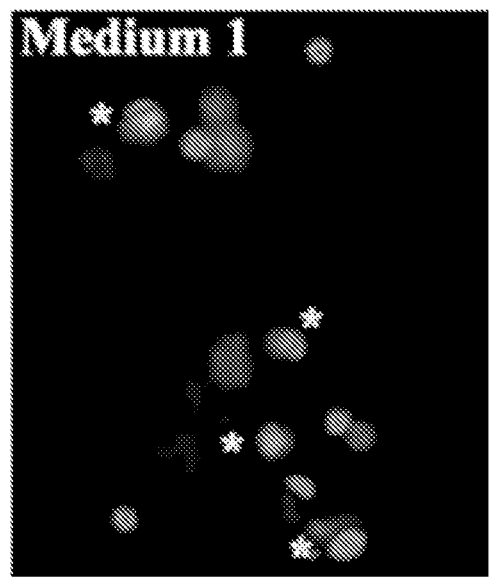
FIG. 13(A) is a microscopic image showing caspase 3/7 activity in MNCs isolated from the peripheral blood of ALS patients. Images show the numbers of Caspase 3/7 positive cells in Medium 1 (Group III) (red, asterisks). The nuclei are stained with Hoechst. Magnification is 20×.
Figure 13B:
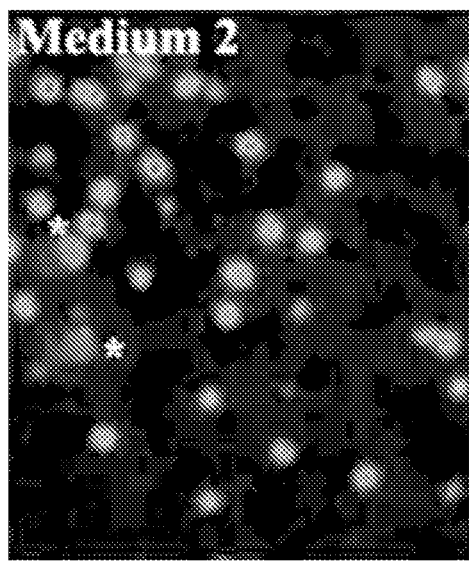
FIG. 13(B) is a microscopic image showing caspase 3/7 activity in MNCs isolated from the peripheral blood of ALS patients. Images show the decreased numbers of Caspase 3/7 positive cells in Medium 2 (Group III) (red, asterisks). The nuclei are stained with Hoechst. Magnification is 20×.

MNCs, isolated from ALS patients, cultured in medium 1 showed many caspase 3/7-positive cells with significantly more pronounced expression in cells compared to controls (p<0.05), as seen in FIG. 11. The increase in caspase-3 and 7-positive cells was more pronounced in in patients with abnormal extensive proliferation (7.38%, Group III), and non-inducible proliferation (5.81%, Group II), compared to patients with "normal" response to PHA (4.58%, Group I) or MNC hUCB (3.75%). Caspase activity of the ALS patients generally showed more activity in patients that exhibited abnormal extensive proliferation or non-inducible proliferation compared to MNCs that showed a normal response to PHA. Using Medium 2 supplemented with hUCB plasma resulted in significantly lower apoptotic activity after a 24-hour incubation for all ALS (p<0.05). However, group analysis suggested that only the Group 1 (ALSFRS <20) and Group 3 (ALSFRS >30) patients had significantly reduced levels of caspase 3/7 (p<0.05; data not shown). When grouped by their response to PHA, only MNCs from patients that exhibited an abnormal response to PHA stimulation, i.e. Groups II and III, showed decreased apoptotic activity (p<0.05) when cultured in Medium 2, as seen in FIG. 12. Images of the stained cells show higher numbers of cells stained positive for caspase 3 & 7 when the cells were incubated in medium 1, seen as asterisk in FIG. 13(A), compared to a decreased number of caspase 3&7 positive cells when grown in medium 2, seen as asterisk in FIG. 13(B).

Figure 14:
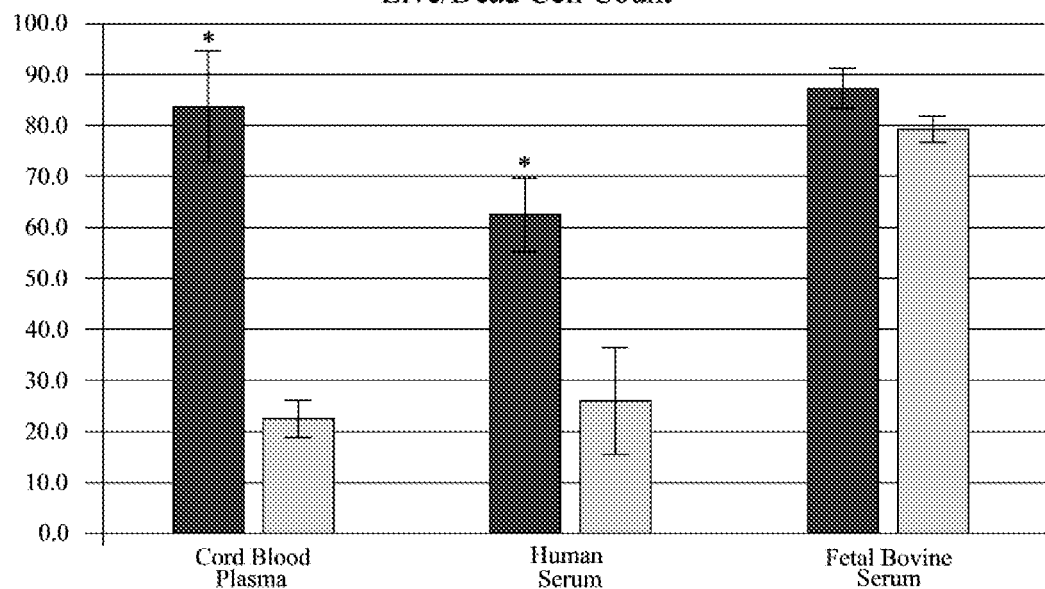
FIG. 14 is a graph showing cord blood plasma decreases cell death in vitro. Human umbilical cord blood cells were cultured in media supplemented with either cord blood plasma (CB Plasma), adult human serum (HS) or fetal bovine serum (FBS). Cells cultured in cord blood plasma demonstrated significantly greater live (dark gray) to dead (light gray) cells, compared to other groups using a Live/Dead viability assay kit. Cord blood plasma provided a beneficial environment that not only supported cell survival with greater viability. Results are plotted as mean±SEM. Statistical significance was determined using two tailed t-tests (* p<0.001).
Figure 15:
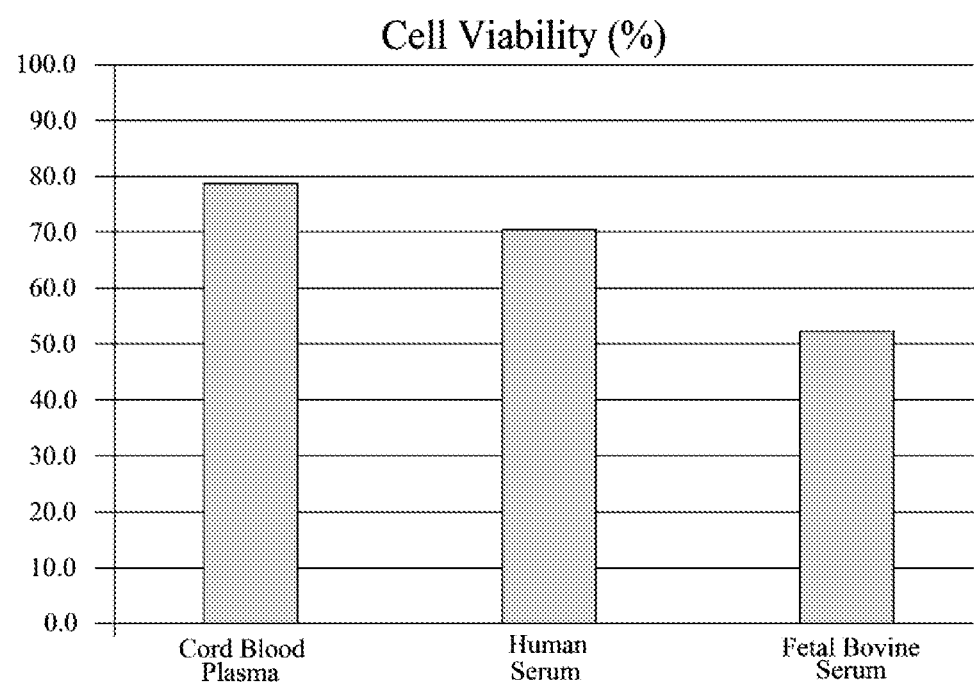
FIG. 15 is a graph showing cord blood plasma decreases cell death in vitro. Human umbilical cord blood cells were cultured in media supplemented with either cord blood plasma (CB Plasma), adult human serum (HS) or fetal bovine serum (FBS). Viability of cells in CB plasma supplemented media was better in comparison to cultures supplemented with either HS or FBS. Cord blood plasma provided a beneficial environment that not only supported cell survival with greater viability.

Cell viability was then tested against other blood serum. hUCB cells were collected as discussed in Example 1. The cells were cultured in media supplemented with cord blood plasma, adult human serum (human serum), or fetal bovine serum (FBS). Cells were incubated for 3 days, followed by a PBS wash and analysis of viability using the commercially available LIVE/DEAD cell viability assay (ThermoFisher Scientific, Cat. No. L3224). Six random fields were selected and images by confocal microscopy for each growth condition. As seen in FIG. 14, cells grown in human serum possessed the lowest number of live cells, with around 62 live cells identified. By comparison, cells grown in cord blood plasma and fetal bovine serum were found to have around 85 live cells and 88 live cells, respectively. The number of dead cells was found to be the highest in fetal bovine serum-supplemented media, followed by human serum and cord blood, at 79 cells, around 25 cells, and around 22 cells, respectively. This resulted in a ratio of live to dead cells of 3.7:1 for cord blood plasma, 2.4:1 for human serum, and 1.1:1 for fetal bovine serum. Cell viability was calculated, following a similar pattern, with cord blood showing viability of around 79%, 70% for human serum, and around 52% for fetal bovine serum, as seen in FIG. 15.

Cord blood plasma decreased apoptotic Caspase 3&7 activity in MNCs isolated from the peripheral blood of patients with both abnormal extensive or non-inducible cell proliferation to the mitogen (PHA).

Example 6

Intravenous administration of hUCB cells delayed the progression of disease and prolonged lifespan in the G93A SOD1 mouse model of ALS (Garbuzova-Davis, et al., Multiple intravenous administrations of human umbilical cord blood cells benefit in a mouse model of ALS. PLoS One 7(2):e31254; 2012; Garbuzova-Davis, et al., Human umbilical cord blood treatment in a mouse model of ALS: optimization of cell dose. PLoS One 3(6):e2494; 2008; Garbuzova-Davis, et al., Intravenous administration of human umbilical cord blood cells in a mouse model of amyotrophic lateral sclerosis: distribution, migration, and differentiation. J. Hematother. Stem Cell Res. 12(3):255-270; 2003). These results were further supported by observations of increased motor neuron survival in both the cervical and lumbar regions of the spinal cord. Also, restored WBC profiles and decreased pro-inflammatory cytokine production were determined. While these results have yet to be replicated in the clinic, the results demonstrate the therapeutic potential of using plasma derived from hUCB to mitigate the mitogen-induced proliferation response of MNCs isolated from the peripheral blood of ALS patients in vitro.

ALS patients differed in lymphocyte functionality, possibly due to differences in the immune response as a consequence of the disease state. The patient with an abnormally extensive cell proliferation in response to mitogen (PHA) in vitro (Group III) may result from an autoimmunity impairment while the non-inducible proliferation patients (Group II) suggests immune deficiency.

This suggests that use of therapies which affect the immune system may not be effective in all patients, suggesting that a more personalized medicine approach may be necessary. A recent clinical study of autologous MSCs as a treatment therapy for ALS suggested that not all patients responded to treatment (Kim, et al., Biological markers of mesenchymal stromal cells as predictors of response to autologous stem cell transplantation in patients with amyotrophic lateral sclerosis: an investigator-initiated trial and in vivo study. Stem Cells 32(10):2724-2731; 2014). A higher secretion of biological markers such as VEGF, angiopoietin and TGF-β was observed from the MSCs of those patients who responded to the treatment and this could be explored further with regards to the observations.

Innate and adaptive immune responses clearly play an important role in ALS. Infiltration of microglia and T cells is evident, and it has been suggested that these cells may initially be protective (Banerjee, et al., Adaptive immune neuroprotection in G93A-SOD1 amyotrophic lateral sclerosis mice. PLoS One 3(7):e2740; 2008; Beers, et al., CD4+ T cells support glial neuroprotection, slow disease progression, and modify glial morphology in an animal model of inherited ALS. Proc. Natl. Acad. Sci. USA 105(40):15558-15563; 2008; Chiu, et al., T lymphocytes potentiate endogenous neuroprotective inflammation in a mouse model of ALS. Proc. Natl. Acad. Sci. USA 105(46):17913-17918; 2008), but some studies have also observed lymphopenia in ALS patients or G93A SOD1 symptomatic mice (Banerjee, et al., Adaptive immune neuroprotection in G93A-SOD1 amyotrophic lateral sclerosis mice. PLoS One 3(7):e2740; 2008; Kuzmenok, et al., Lymphopenia and spontaneous autorosette formation in SOD1 mouse model of ALS. J. Neuroimmunol. 172(1-2):132-136; 2006; Provinciali, et al., Immunity assessment in the early stages of amyotrophic lateral sclerosis: a study of virus antibodies and lymphocyte subsets. Acta Neurol. Scand. 78(6):449-454; 1988). However, the precise roles of the immune responses, whether causative and/or a consequence of the disease still need to be determined (Murdock, et al., The dual roles of immunity in ALS: injury overrides protection. Neurobiol. Dis. 77:1-12; 2015; Rodrigues, et al., The innate and adaptive immunological aspects in neurodegenerative diseases. J. Neuroimmunol. 269(1-2):1-8; 2014). While there is no doubt that the immune system is involved in ALS, it is worth noting that immunosuppressive therapies for ALS are not very effective (Pagani, et al., Autoimmunity in amyotrophic lateral sclerosis: past and present. Neurol. Res. Int. 2011:497080; 2011). There is evidence for autoimmunity being a component of ALS, though it is unclear whether it is causative or an epiphenomenon (Alexianu, The role of immune processes in amyotrophic lateral sclerosis pathogenesis. Rom. J. Neurol. Psychiatry 33(3-4):215-227; 1995; Appel, et al., Autoimmunity as an etiological factor in sporadic amyotrophic lateral sclerosis. Adv. Neurol. 68:47-57; 1995; Coban, et al., Serum anti-neuronal antibodies in amyotrophic lateral sclerosis. Int. J. Neurosci. 123(8):557-562; 2013; Niebroj-Dobosz, et al., Auto-antibodies against proteins of spinal cord cells in cerebrospinal fluid of patients with amyotrophic lateral sclerosis (ALS). Folia Neuropathol. 44(3):191-196; 2006; Pagani, et al., Autoimmunity in amyotrophic lateral sclerosis: past and present. Neurol. Res. Int. 2011:497080; 2011; Rodrigues, et al., The innate and adaptive immunological aspects in neurodegenerative diseases. J. Neuroimmunol. 269(1-2):1-8; 2014), with some suggestion that autoimmunity could be beneficial in chronic neuroinflammation (Schwartz & Baruch, Breaking peripheral immune tolerance to CNS antigens in neurodegenerative diseases: boosting autoimmunity to fight-off chronic neuroinflammation. J. Autoimmun. 54:8-14; 2014). Serum, CSF and immune cells from ALS patients has also been shown to contain increased levels of IL-17 and IL-23, which may be a sign of T helper 17 (Th17) cell activation—a cell type that may play a crucial role in destructive autoimmunity (Fiala, et al., IL-17A is increased in the serum and in spinal cord CD8 and mast cells of ALS patients. J. Neuroinflammation 7:76; 2010; Rentzos, et al., Interleukin-17 and interleukin-23 are elevated in serum and cerebrospinal fluid of patients with ALS: a reflection of Th17 cells activation? Acta Neurol Scand. 122(6):425-429; 2010; Saresella, et al., T helper-17 activation dominates the immunologic milieu of both amyotrophic lateral sclerosis and progressive multiple sclerosis. Clin. Immunol. 148(1):79-88; 2013).

While the study demonstrated impairment of mononuclear cells obtained from the peripheral blood of ALS patients via mitogen induction, Bossolasco et al. (Bossolasco, et al., Metalloproteinase alterations in the bone marrow of ALS patients. J. Mol. Med. 88(6):553-564; 2010) have detected impaired functionality of bone marrow stem cells (BMSCs) from ALS patients in the ability to proliferate and differentiate into adipogenic and osteoblastic tissue, though Ferrero et al. (Ferrero, et al., Bone marrow mesenchymal stem cells from healthy donors and sporadic amyotrophic lateral sclerosis patients. Cell Transplant. 17(3):255-266; 2008) noted no significant differences in the proliferation potential of bone marrow mesenchymal stem cells from ALS patients. Liu and Martin (Liu, & Martin, The adult neural stem and progenitor cell niche is altered in amyotrophic lateral sclerosis mouse brain. J. Comp. Neurol. 497(3):468-88; 2006) showed a similar impairment of neural stem cells (NSCs) in the subventricular zone of symptomatic G93A SOD1 mice. These studies suggested that some cell populations, such as the peripheral blood lymphocytes and possibly the BMSCs, undergo changes in their ability to proliferate and/or differentiate in ALS patients, however, no reports exist to confirm any abnormal cell function. Though Kang et al. (Kang, et al., Degeneration and impaired regeneration of gray matter oligodendrocytes in amyotrophic lateral sclerosis. Nat. Neurosci. 16(5):571-579; 2013) have detected enhanced proliferation of non-stimulated oligodendrocytic progenitors in the G93A SOD1 transgenic mouse.

The findings demonstrated that cord blood plasma was effective at modulating the cell response to PHA in the patient with abnormally extensive cell proliferation (Group III) as well as the patients with non-inducible cell proliferation (Group II), but not the patients who responded normally (Group I). Also, hUCBP decreased apoptotic Caspase 3/7 activity in MNCs isolated from the peripheral blood of patients with both abnormal extensive or non-inducible cell proliferation to the mitogen (PHA). Additionally, when standard media (Medium 1) was replaced with media containing hUCBP (Medium 2) the apoptotic activity of the MNCs in culture tended to decrease. These findings reinforce the current anti-inflammatory observations that have been made of hUCB cells (Garbuzova-Davis, et al., Multiple intravenous administrations of human umbilical cord blood cells benefit in a mouse model of ALS. PLoS One 7(2): e31254; 2012), and also demonstrate that plasma derived from cord blood could be an effective treatment in ALS patients with immune dysfunction as an immune-modulator and/or anti-apoptotic factor.

ALSFRS/ALSFRS-R scoring of ALS patients is a well-recognized and widely used standard in ALS clinics to validate patient disease stage. Although the testing methodology might be subjective, all the data was collected by the same neurologist in order to minimize the potential for bias. The scores were then calculated using the on-line ALS C.A.R.E. program (Center for Outcomes Research, Univ Massachusetts Medical School, 2015).

Although the patient sample size in the study was modest, it was sufficient to provide a valid analysis of hUCB plasma effects on mitogen-induced proliferation of MNCs isolated from the peripheral blood of ALS patients. Additionally, the significant reduction of apoptotic activity of these cells via hUCB plasma is an important study finding.

The therapeutic uses of hUCB plasma (hUCBP) are shown for ALS. hUBCP modulates immune cell response to stimulation with the mitogen PHA. Also, hUCBP is a novel therapy that appears to correct any immunological issues that arise from ALS. This therapy can be combined with hUCB cell (or other cell) transplants to potentially help provide a more supportive environment for the transplanted cells.

Example 7

In development of alternative approaches in treatment for age-related diseases, proteins from "young" blood have been intensely investigated. Studies of parabiosis, with shared blood circulatory systems between old (16-20 months of age) and young (2-3 months of age) mice, have shown significantly improved cognition and physical function in both aged wild-type mice14 and a mouse model of Alzheimer's disease (AD). (Villeda S A, Plambeck K E, Middeldorp J, et al. Young blood reverses age-related impairments in cognitive function and synaptic plasticity in mice. *Nat Med.* 2014; 20:659-663; Middeldorp J, Lehallier B, Villeda S A, et al. Preclinical assessment of young blood plasma for Alzheimer disease. *JAMA Neurol.* 2016; 73:1325-1333). Middeldorp et al demonstrated that parabiosis of young wild-type mice with AD mice for 5 weeks effectively improved learning and memory while also reducing inflammation in AD mice. (Middeldorp J, Lehallier B, Villeda S A, et al. Preclinical assessment of young blood plasma for Alzheimer disease. *JAMA Neurol.* 2016; 73:1325-1333). Additionally, the authors noted increased synaptic activity in the hippocampus of AD mice. Based on these study results, clinical trial (NCT02256306) investigated the safety of 4-weekly infusions of young blood plasma from donors aged between 18 and 30 years of age into patients with AD. Although no serious adverse reactions occurred, the study found no significant effect on patient cognition but did show significant improvements in daily living skills.

Although results of using young blood are promising, it is still unclear which constituents of "young" blood are providing beneficial effects. Potentially, paracrine actions are involved in positive outcomes for treatment of an age-related disease such as AD. Also, hormonal status of donors should be investigated due to the wide age range (18-30 years) of donors. Alternatively, plasma derived from hUCB could be a more beneficial therapeutic due to its unique and uniform molecular composition.

In the present study, various factors in CBP derived from hUCB and the effect of CBP on mononuclear cells isolated from hUCB (MNC hUCB) in vitro were evaluated in the context of establishing CBP as a potential therapeutic agent.

Cytokine and growth factor profiles were examined within the same samples of CBP and human adult blood plasma/sera (ABP/S). The effect of autologous CBP on MNC hUCB in vitro was determined and compared to ABP/S and standard FBS media supplements. The major study findings were that CBP demonstrated: (a) significantly "low" concentrations of the proinflammatory cytokines IL-2, IL-6, IFN-γ, and TNF-α; (b) significantly "low" concentrations of immunomodulatory IL-5 cytokine and GM-CSF; (c) significantly "elevated" level of the chemokine IL-8; (d) significantly high concentrations of VEGF, G-CSF, EGF and FGF-basic growth factors; (e) significantly "increased" viability of MNC hUCB in vitro with autologous CBP media supplement; and (f) significantly "decreased" apoptotic MNC hUCB in vitro with autologous CBP media supplement.

The inventors are the first to demonstrate the unique CBP composition of cytokines and growth factors within the same samples, providing evidence of the unique protein content in CBP. Also, the inventors found that autologous CBP promoted MNC hUCB viability and reduced apoptotic cell death in vitro, supporting the notion that CBP has potential as a sole therapeutic or cell-additive agent in developing clinically relevant CBP-based therapies for various neurodegenerative diseases.

It has been shown that in addition to a high concentration of growth factors, human CBP also contains a great amount of soluble proliferative and immunomodulatory factors such as (TGF)-β, G-CSF, GM-CSF, monocyte chemoattractant protein (MCP)-1, IL-6, and IL-8.17 Also, IL-16 cytokine, a modulator of T cell activation, has been detected in CBP18 and potentially presents a physiological mechanism for fetal-maternal tolerance. (Tekkatte C, Gunasingh G P, Cherian K M, Sankaranarayanan K. "Humanized" stem cell culture techniques: the animal serum controversy. *Stem Cells Int.* 2011). Due to CBP's specific molecular composition, numerous studies showed beneficial effect of CBP in replacement of standard FBS for various cell expansions in vitro, which may be essential to achieve appropriate cell numbers for clinical use. (Ding Y, Yang H, Feng J B, et al. Human umbilical cord-derived MSC culture: the replacement of animal sera with human cord blood plasma. *In Vitro Cell Dev Biol Anim.* 2013; 49:771-777; Lee J-Y, Nam H, Park Y-J, et al. The effects of platelet-rich plasma derived from human umbilical cord blood on the osteogenic differentiation of human dental stem cells. *In Vitro Cell Dev Biol Anim.* 2011; 47:157-164; Kim Y-M, Jung M-H, Song H-Y, et al. Ex vivo expansion of human umbilical cord blood-derived T-lymphocytes with homologous cord blood plasma. *Tohoku J Exp Med.* 2005; 205:115-122; Huang L, Critser P J, Grimes B R, Yoder M C. Human umbilical cord blood plasma can replace fetal bovine serum for in vitro expansion of functional human endothelial colony-forming cells. *Cytotherapy.* 2011; 13:712-721).

In the current study, cytokine and growth factor levels were analyzed in the same CBP samples for a better understanding of CBP molecular composition prior to proposing CBP as a therapeutic agent. The inventors showed low concentrations of pro-inflammatory IL-2, IL-6, IFN-γ and TNF-α cytokines in CBP, presumably secreted by various cells in hUCB, which signify the immune immaturity of these cell populations.

Additionally, the study findings demonstrated a significantly low concentration of immunomodulatory cytokine IL-5 in CBP vs. ABP/S, supporting previous study results. (Garanina E E, Gatina D, Martynova E V, et al. Cytokine profiling of human umbilical cord plasma and human umbilical cord blood mononuclear cells. *Blood.* 2017; 130: 4814). This cytokine, mainly produced by Th2 helper lymphocytes and mast cells, promotes growth/differentiation of B cells and granulocytes upon immunological and/or antigenic priming in development of the adaptive immune response. However, increased concentrations of IL-5, IL-2 and transcription factor GATA-4 determined in CBP may result in abnormal patterns of fetal immune system development and induce risk of allergic disease. (Marschan E, Honkanen J, Kukkonen K, et al. Increased activation of GATA-3, IL-2 and IL-5 of cord blood mononuclear cells in infants with IgE sensitization. *Pediatr Allergy Immunol.* 2008; 19:132-139).

Also, it has been shown that antioxidant capacity, evaluated by carbonyl levels in CBP, was significantly higher in patients delivering neonates by caesarean vs. vaginal route, suggesting that the delivery method impacts oxidative stress. (Noh E J, Kim Y H, Cho M K, et al. Comparison of oxidative stress markers in umbilical cord blood after vaginal and cesarean delivery. *Obstet Gynecol Sci.* 2014; 57:109-114). In the present study, the low concentration of GM-CSF found in CBP together with the low concentrations of pro-inflammatory cytokines provide further evidence of anti-inflammatory hUCB content. Thus, low levels of pro-inflammatory and immunomodulatory cytokines in CBP provide a favorable microenvironment for cellular content in hUCB. It has been shown that transplantation of MNC derived from hUCB even from unrelated donors into patients with hematologic malignancies causes a low incidence of graft-versus-host disease compared to bone marrow or peripheral blood cell administration. (Zhang H, Chen J, Que W. A meta-analysis of unrelated donor umbilical cord blood transplantation versus unrelated donor bone marrow transplantation in acute leukemia patients. *Biol Blood Marrow Transplant.* 2012; 18:1164-1173; Chen Y, Xu L, Liu D, et al. Comparative outcomes between cord blood transplantation and bone marrow or peripheral blood stem cell transplantation from unrelated donors in patients with hematologic malignancies: a single-institute analysis. *Chin Med J.* 2013; 126:2499-2503).

The present study results also demonstrated similar amounts of anti-inflammatory IL-4 and IL-10 cytokines in CBP and ABP/S, However, it is important to note that these anti-inflammatory cytokines were present at a greater concentration than the pro-inflammatory constituents of CBP, suggesting a favorable cytokine composition towards developing CBP as potential therapeutic agent. Since IL-10 is an important cytokine for downregulation of Th1 inflammatory cytokines and MHC class II antigens, a decrease of this cytokine is mainly associated with altered cell-mediated immunosuppression and induction of complications during pregnancy. (Mobini M, Mortazavi M, Nadi S, et al. Significant roles played by interleukin-10 in outcome of pregnancy. *Iran J Basic Med Sci.* 2016; 19:119-124). In contrast, increased cord blood IL-10 was determined in preterm infants compared to full-term newborns. (Blanco-Quirós A, Arranz E, Solis G, et al. Cord blood interleukin-10 levels are increased in preterm newborns. *Eur J Pediatr.* 2000; 159: 420-423; Blanco-Quirós A, Arranz E, Solis G, et al. High cord blood IL-10 levels in preterm newborns with respiratory distress syndrome. *Allergol Immunopathol (Madr).* 2004; 32:189-196). In the current study, hUCB units were used from healthy infants delivered naturally, so IL-10 levels determined in CBP vs. ABP/S likely reflect steady immune/inflammatory humoral status in hUCB.

Amongst the additional important study findings were significant elevations of VEGF, G-CSF, EGF and FGF-basic growth factors in CBP vs. ABP/S. Both EGF and FGF-basic promote stem cell renewal and inhibit cell senescence and elevated levels of EGF largely correlate to gestational age and birth weight of the developing fetus. (Coutu D L, Galipeau J. Roles of FGF signaling in stem cell self-renewal, senescence and aging. *Aging (Albany NY).* 2011; 3:920-933; Ichiba H, Fujimura M, Takeuchi T. Levels of epidermal growth factor in human cord blood. *Biol Neonate.* 1992; 61:302-307; Wahab Mohamed W A, Aseeri A M. Cord blood epidermal growth factor as a possible predictor of necrotizing enterocolitis in very low birth weight infants. *J Neonatal Perinatal Med.* 2013; 6:257-262). Thus, the increased levels of EGF and FGF-basic in CBP determined in the study may indicate normal fetal development. Also, increased G-CSF, a bone marrow stem cell mobilizing factor, in CBP potentially reflects intensive production of bone marrow derived stem cells in the fetus. The combination of this growth factor with MNC hUCB for the treatment of myeloid malignancies in human adults after radiation promoted cell engraftment in bone marrow replacement therapies. (Delaney C, Ratajczak M Z, Laughlin M J. Strategies to enhance umbilical cord blood stem cell engraftment in adult patients. *Expert Rev Hematol.* 2010; 3:273-283; Broxmeyer H E, Hangoc G, Cooper S, et al. Growth characteristics and expansion of human umbilical cord blood and estimation of its potential for transplantation in adults. *Proc Natl Acad Sci USA.* 1992; 89:4109-4113). Also, co-administration of G-CSF with MNC hUCB into an animal model of traumatic brain injury results demonstrated reduction of neuroinflammation and promotion of stem cells into the injured side of the brain. (De La Peña I, Sanberg P R, Acosta S, et al. G-CSF as an adjunctive therapy with umbilical cord blood cell transplantation for traumatic brain injury. *Cell Transplant.* 2015; 24:447-457).

Of note, significantly elevated levels of the chemokine IL-8 and VEGF were determined in CBP vs. ABP/S in the current study. While IL-8 is primarily known as a pro-inflammatory mediator, it also recognized as a promoter of angiogenic activity as demonstrated by endothelial cell survival, proliferation and migration in vitro. (Li A, Dubey S, Varney M L, et al. IL-8 directly enhanced endothelial cell survival, proliferation, and matrix metalloproteinases production and regulated angiogenesis. *J Immunol.* 2003; 170: 3369-3376; Lai Y, Liu X H, Zeng Y, et al. Interleukin-8 induces the endothelial cell migration through the Rac 1/RhoA-p38MAPK pathway. *Eur Rev Med Pharmacol Sci.* 2012; 16:630-638). Interestingly, the concentration of the angiogenic VEGF growth factor was also significantly higher in CBP vs. ABP/S. It is possible that the elevated level of VEGF is a result of the high concentration of IL-8, which promotes increased expression of VEGF by endothelial cells. (Martin D, Galisteo R, Gutkind J S. CXCL8/IL8 stimulates vascular endothelial growth factor (VEGF) expression and the autocrine activation of VEGFR2 in endothelial cells by activating NFkappaB through the CBM (Carma3/Bcl10/Malt1) complex. *J Biol Chem.* 2009; —284: 6038-6042; Li M, Zhang Y, Feurino L W, et al. Interleukin-8 increases vascular endothelial growth factor and neuropilin expression and stimulates ERK activation in human pancreatic cancer. *Cancer Sci.* 2008; 99:733-737). A recently published study demonstrated that microRNA-containing exosomes derived from maternal and umbilical cord serum dramatically promote human umbilical vein endothelial cell proliferation, migration, and tube formation in vitro, highlighting the important role of exosomes in the regulation of angiogenesis during gestation. (Jia L, Zhou X, Huang X, et al. Maternal and umbilical cord serum derived exosomes enhance endothelial cell proliferation and migration. *FASEB J.* 2018). Exclusively, VEGF has been studied for potential therapeutic efficacy in animal models of ALS and its use in clinical settings has been discussed (Lambrechts D, Storkebaum E, Carmeliet P. VEGF: necessary to prevent motoneuron degeneration, sufficient to treat ALS? *Trends Mol Med.* 2004; 10:275-282; Pronto-Laborinho A C, Pinto S, de Carvalho M. Roles of vascular endothelial growth factor in amyotrophic lateral sclerosis. *Biomed Res Int.* 2014; Keifer O P, O'Connor D M, Boulis N M. Gene and protein therapies utilizing VEGF for ALS. *Pharmacol Ther.* 2014; 141:261-271). Nevertheless, CBP containing high levels of IL-8 and VEGF might be a beneficial treatment for repair of the damaged blood-brain barrier and/or blood-spinal cord barrier in patients with ALS, AD, Parkinson's disease and multiple sclerosis. (Garbuzova-Davis S, Hernandez-Ontiveros D G, Rodrigues M C O, et al. Impaired blood-brain/spinal cord barrier in ALS patients. *Brain Res.* 2012; 1469: 114-128; Garbuzova-Davis S, Sanberg P R. Blood-CNS barrier impairment in ALS patients versus an animal model. *Front Cell Neurosci.* 2014; 8:21; Henkel J S, Beers D R, Wen S, et al. Decreased mRNA expression of tight junction proteins in lumbar spinal cords of patients with ALS. *Neurology.* 2009; 72:1614-1616; Winkler E A, Sengillo J D, Sullivan J S, et al. Blood-spinal cord barrier breakdown and pericyte reductions in amyotrophic lateral sclerosis. *Acta Neuropathol.* 2013; 125:111-120; Goos J D C, Teunissen C E, Veerhuis R, et al. Microbleeds relate to altered amyloid-O metabolism in Alzheimer's disease. *Neurobiol Aging.* 2012; Kortekaas R, Leenders K L, van Oostrom J C H, et al. Blood-brain barrier dysfunction in parkinsonian midbrain in vivo. *Ann Neurol.* 2005; 57:176-179; Stone L A, Smith M E, Albert P S, et al. Blood-brain barrier disruption on contrast-enhanced MRI in patients with mild relapsing-remitting multiple sclerosis: relationship to course, gender, and age. *Neurology.* 1995; 45:1122-1126).

Finally, the in vitro studies showed significantly increased viability of MNC hUCB when autologous CBP was added to culture media. Also, apoptotic activity of MNC hUCB in vitro, determined by TUNEL, was also decreased after autologous CBP exposure compared to cultures supplemented with ABP/S or FBS. Supporting this novel finding, the previous study demonstrated reduced activities of other pro-apoptotic factors, such as caspase 3/7, from ALS patient-derived MNC's cultured in media supplemented with CBP. (Eve D J, Ehrhart J, Zesiewicz T, et al. Plasma Derived From Human Umbilical Cord Blood Modulates Mitogen-Induced Proliferation of Mononuclear Cells Isolated From the Peripheral Blood of ALS Patients. *Cell Transplant.* 2016; 25:963-971). In this context, numerous studies have shown neuroprotective effects of MNC hUCB administered into animal models of ALS, AD, Parkinson's disease, ischemic stroke and traumatic brain injury. (Ende N, Weinstein F, Chen R, Ende M. Human umbilical cord blood effect on sod mice (amyotrophic lateral sclerosis). *Life Sci.* 2000; 67:53-59; Garbuzova-Davis S, Willing A E, Zigova T, et al. Intravenous administration of human umbilical cord blood cells in a mouse model of amyotrophic lateral sclerosis: distribution, migration, and differentiation. *J Hematother Stem Cell Res.* 2003; 12:255-270; Garbuzova-Davis S, Sanberg C D, Kuzmin-Nichols N, et al. Human umbilical cord blood treatment in a mouse model of ALS: optimization of cell dose. *PLoS ONE.* 2008; Garbuzova-Davis S, Rodrigues M C O, Mirtyl S, et al. Multiple intravenous administrations of human umbilical cord blood cells benefit in a mouse model of ALS. *PLoS ONE.* 2012; Nikolic W V, Hou H, Town T, et al. Peripherally administered human umbilical cord blood cells reduce parenchymal and vascular beta amyloid deposits in Alzheimer mice. *Stem Cells Dev.* 2008; 17:423-439; Darlington D, Deng J, Giunta B, et al. Multiple low-dose infusions of human umbilical cord blood cells improve cognitive impairments and reduce amyloid-β-associated neuropathology in Alzheimer mice. *Stem Cells Dev.* 2013; 22:412-421; Darlington D, Li S, Hou H, et al. Human umbilical cord blood-derived monocytes improve cognitive deficits and reduce amyloid-O pathology in PSAPP mice. *Cell Transplant.* 2015; 24:2237-2250; Abo-Grisha N, Essawy S, Abo-Elmatty D M, Abdel-Hady Z. Effects of intravenous human umbilical cord blood CD34+ stem cell therapy versus levodopa in experimentally induced Parkinsonism in mice. *Arch Med Sci.* 2013; 9:1138-1151; Newcomb J D, Ajmo C T, Sanberg C D, et al. Timing of cord blood treatment after experimental stroke determines therapeutic efficacy. *Cell Transplant.* 2006; 15:213-223; Boltze J, Schmidt U R, Reich D M, et al. Determination of the therapeutic time window for human umbilical cord blood mononuclear cell transplantation following experimental stroke in rats. *Cell Transplant.* 2012; 21:1199-1211; Acosta S A, Tajiri N, Shinozuka K, et al. Combination therapy of human umbilical cord blood cells and granulocyte colony stimulating factor reduces histopathological and motor impairments in an experimental model of chronic traumatic brain injury. *PLoS ONE.* 2014; Min K, Song J, Lee J H, et al. Allogenic umbilical cord blood therapy combined with erythropoietin for patients with severe traumatic brain injury: three case reports. *Restor Neurol Neurosci.* 2013; 31:397-410). However, insignificant numbers of MNC hUCB were detected in the CNS of these animal models after intravenous cell administration. This scarcity is likely due to a low rate of cell survival, since cell preparation and injection involve dilution with a basic buffer solution. Substitution of this diluent with autologous CBP presents a more supportive microenvironment for cell survival and increases therapeutic efficacy of administered MNC hUCB. Especially, complementing MNC hUCB with autologous CBP may foster injected cell survival as supported by the in vitro study results on cell viability and apoptotic activity. Also, repeated administrations of MNC hUCB cells with autologous CBP may prove even more advantageous. Alternatively, injection of non-autologous CBP alone can be efficacious for treatment of various neurodegenerative diseases and/or aging population per se. Beneficial effects have been observed from intravenous administration of CBP into rats modelling acute ischemic stroke or into an animal model of aging. (Yoo J, Kim H-S, Seo J-J, et al. Therapeutic effects of umbilical cord blood plasma in a rat model of acute ischemic stroke. *Oncotarget.* 2016; 7:79131-79140; Castellano J M, Mosher K I, Abbey R J, et al. Human umbilical cord plasma proteins revitalize hippocampal function in aged mice. *Nature.* 2017; 544:488-492). In these studies, multiple injections of CBP were performed and this therapeutic approach needs to be considered. In agreement with this approach, repeated deliveries of CBP could provide ongoing trophic support for damaged cells and/or tissues. The inventors showed that CBP is a potential therapeutic due to its unique composition. The inventors examine the effect of CBP alone and in combination with MNC hUCB for treatment of ALS using a symptomatic animal model of disease for a translational perspective.

Results

Cord Blood Plasma Cytokine Profile

Figure 16:
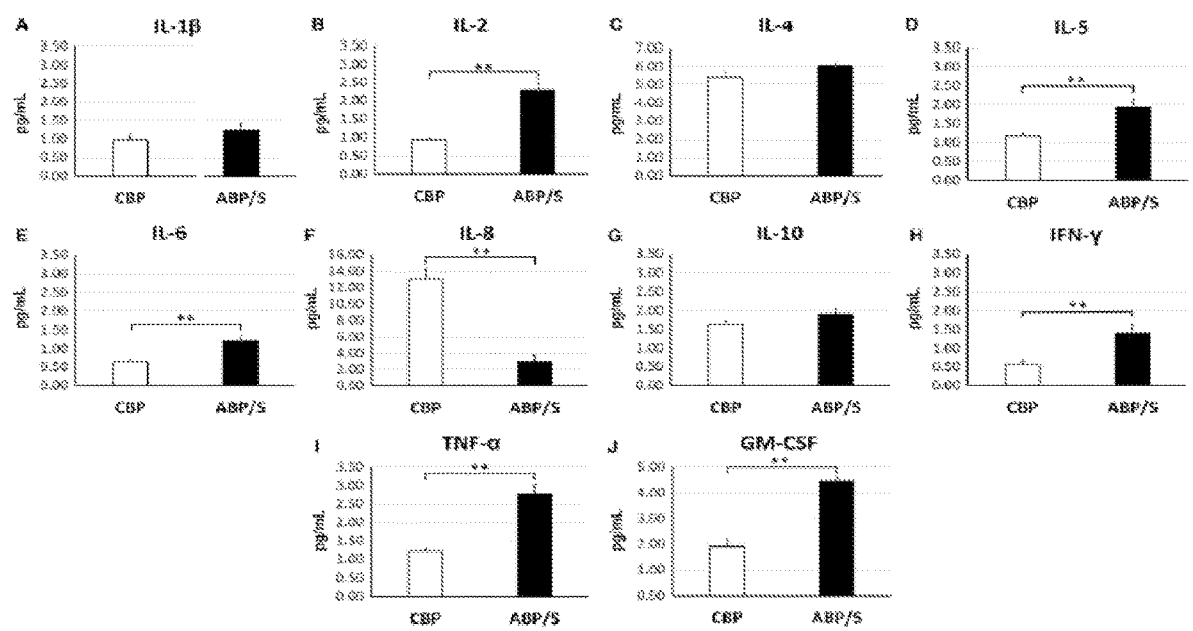
FIG. 16A-J is a series of graphs depicting cord blood plasma cytokine profile. The cytokine profiles of CBP (n=20) and ABP/S (n=6) were assayed using an ultrasensitive human cytokine panel in triplicate. Significantly lower concentrations of the pro-inflammatory cytokines (B) IL-2, (E) IL-6, (H) IFN-γ and (I) TNF-α were detected in CBP vs. ABP/S. Levels of immunomodulatory (D) IL-5 cytokine and (J) GM-CSF were significantly low in CBP. A significant increase in (F) IL-8 was also determined in CBP. There were no significant differences between CBP and ABP/S for (A) IL-1β, (C) IL-4 and (G) IL-10. **P<0.01

Samples of CBP and ABP/S were assayed to determine cytokine profiles using an ultrasensitive human cytokine 10-plex panel. Results showed significantly ($P<0.01$) lower concentrations of the proinflammatory cytokines IL-2, IFN-γ and TNF-α in CBP compared to ABP/S (FIG. 16B, H,I). Additionally, levels of immunomodulatory IL-5 (FIG. 16D) and multifunctional IL-6 (FIG. 16E) cytokines were also significantly ($P<0.01$) lower in CBP vs. ABP/S. Significantly ($P<0.01$) elevated concentrations of the chemokine IL-8 were determined in CBP in comparison in ABP/S (FIG. 16F). Interestingly, levels of the pro-inflammatory immune cell maturating factor, GMCSF, were significantly ($P<0.01$) lower in CBP than in ABP/S (FIG. 16J). Although the levels of IL-1β, IL-4 and IL-10 were slightly reduced in CBP compared to ABP/S, these reductions were not statistically significant ($P>0.05$) (FIG. 16A,C,G). While anti-inflammatory IL-4 and IL-10 cytokine concentrations were not significantly different between CBP and ABP/S, it is important to note that most of the pro-inflammatory cytokines within CBP were present at lower concentrations than their anti-inflammatory counterparts. Concentrations of cytokines in CBP and ABP/S are provided in Table 1A of FIG. 17.

Cord Blood Plasma Growth Factor Profile

The levels of several common growth factors were measured in CBP and ABP/S using a human growth factor four-plex assay. The concentrations of VEGF were significantly ($P<0.01$) higher in CBP, more than two-fold, vs. ABP/S (FIG. 18A). The concentrations of G-CSF, a bone marrow stem cell stimulating growth factor, were also significantly ($P<0.05$) higher in CBP compared to ABP/S (FIG. 18B). Also, the cell proliferating growth factors: epidermal growth factor (EGF) and fibroblast growth factor basic (FGF-basic) were significantly ($P<0.01$) elevated in CBP (FIG. 18C,D; respectively). Of note, the levels of EGF and FGF-basic factors were about 2.5-fold higher in CBP vs. ABP/S. Levels of growth factors in CBP and ABP/S are indicated in Table 1B of FIG. 17.

Viability of MNC hUCB Cultured with Autologous CBP

Cryopreserved MNC hUCB was incubated with RPMI-1640 media supplemented with autologous CBP, ABP/S, or FBS for 5 days. After 5 days in vitro, the cells were stained using the LIVE/DEAD Viability/Cytotoxicity assay to identify the viable (dark grey) and non-viable cytotoxic cell populations (light grey). Numerous viable MNC hUCB were observed in cultures with CBP (FIG. 19Aa) and FBS (FIG. 19Ac) supplements. Fewer viable cells were seen with ABP/S (FIG. 19Ab) added into media. Live cell counts of MNC hUCB supplemented with autologous CBP were significantly ($83.83 \pm 10.86$ cell number, $P<0.05$) higher vs. cultured cells supplemented with ABP/S ($60.35 \pm 5.50$ cell number, FIG. 19B). However, numbers of viable cells cultured with CBP ($83.83 \pm 10.86$ cell number) and FBS ($87.33 \pm 7.17$ cell number) were similar (FIG. 19B). Importantly, media supplemented with CBP showed significantly ($P<0.01$) reduced numbers of dead MNC hUCB ($22.50 \pm 3.67$ cell number) compared to FBS ($79.33 \pm 10.48$ cell number). Yet, MNC hUCB cultured with FBS demonstrated a significant ($P<0.05$) increase of dead cells vs. cultured cells supplemented with ABP/S (38.15±6.90 cell number, FIG. 19B). Additionally, cells supplemented in media with CBP had a greater ratio of live to dead cells (3.7:1) compared to cultures that received ABP/S (1.6:1) or FBS (1.1:1).

Apoptotic Activity of MNC hUCB Cultured with Autologous CBP

Apoptotic activity of cultured MNC hUCB in media supplemented with autologous CBP, ABP/S, or FBS was analyzed on day 5 in vitro using a colormetric TUNEL assay. The percentage of apoptotic cells cultured with CBP was significantly lower (17.39±1.70%) compared to cultures supplemented with ABP/S (34.72±2.61%,P<0.001) or FBS (26.62±2.08%, P<0.01) (FIG. 20A). Interestingly, MNC hUCB cultured in media containing FBS showed significantly (P<0.05) lower apoptotic activity vs. cultured cells with ABP/S. Phase contrast microscopic images of MNC hUCB in vitro demonstrated a few cells with abnormal morphology displaying dislocated nuclei in cultures supplemented with CBP (FIG. 20Ba) compared to numerous morphologically damaged cells cultured with ABP/S (FIG. 20Bb) or FBS (FIG. 20Bc), supporting apoptotic cell counts.

Materials and Methods

The human umbilical cord blood (hUCB) units were collected by Texas Cord Blood Bank (TCBB, GenCure, West San Antonio, TX, USA) and provided to Saneron CCEL Therapeutics, Inc. for research purposes. The cord blood units were obtained from full-term pregnancies by vaginal delivery. The umbilical cord blood units were received within 48 hours of collection. Maternal blood samples, collected as the same time as the cord blood, were tested by TCBB for infectious disease markers of HIV, hepatitis B and C, syphilis, CMV and HTLV I&II, and test results were provided for validation of the cord blood units. Each cord blood unit in the study was negative for all infectious disease markers as determined in maternal blood. Human adult blood plasma or sera (ABP/S) was obtained from a commercially available source (Sigma-Aldrich, St. Louis, MO, USA). Upon receipt of ABP/S, samples were aliquoted and stored at −20° C.

Human Umbilical Cord Blood Processing and Plasma Isolation

Human umbilical cord blood (hUCB) units (n=20), with maternal blood samples negative for all tested infectious markers, were processed to obtain an autologous CBP fraction and mononuclear cell population (MNC hUCB, U-CORD-CELL™, Saneron CCEL Therapeutics, Inc., Tampa, FL, USA) as detailed below. Upon receipt, the cord blood units were diluted (1:1) with sterile phosphate buffered saline (PBS) without Mg2+ or Ca2+ (Sigma-Aldrich, St. Louis, MO, USA). The cord blood was then fractionated using the density gradient solution Ficoll (Ficoll-Paque Premium: 1.078 g/mL, Cat. No. 17544202; Millipore Sigma, St. Louis, MO, USA) in the Sepax 2 fully automated cell processing system (Biosafe America Inc., Houston, TX, USA). This allowed for the sterile collection of both CBP and MNC hUCB from each unit of cord blood. The CBP was further centrifuged at 3000 g for 10 minutes to remove any additional red blood cells. The CBP was then aliquoted and stored at −20° C. The MNC hUCB cell numbers and viability were determined using the Vi-CELL Viability Analyzer (Beckman Coulter, Brea, CA, USA). MNC hUCB was then frozen at $5 \times 10^7$ cells per vial using a proprietary cryopreservation media (Saneron CCEL Therapeutics, Inc.) and stored in liquid nitrogen.

Cytokine Profile in Human Umbilical Cord Blood Plasma

A human ultrasensitive cytokine 10-plex panel (Invitrogen, Carlsbad, CA, USA; Cat. No. LHC6004) was used as previously described13 to determine the concentrations of cytokines within CBP (n=20) and ABP/S (n=6) in triplicate, following the manufacturer's protocol. All measurements were performed by an investigator blinded to the sample source. Granulocyte-macrophage colony-stimulating factor (GM-CSF) and cytokine levels of interleukin (IL)-1β, IL-2, IL-4, IL-5, IL-6, IL-8, IL-10, interferon-gamma (IFN-γ), tumor necrosis factor alpha (TNF-α) and GM-CSF were quantified using the Bio-Rad Bio-Plex® Luminex 200 multiplex assay system (Bio-Rad Laboratories Inc., Hercules, CA, USA). The Bio-Rad Bio-Plex® 200 software (BioRad Laboratories Inc., Hercules CA, USA) was used to calculate the sample cytokine concentrations according to a standard curve and results were presented as picograms of analyte per milliliter (μg/mL).

Growth Factor Profile in Human Umbilical Cord Blood Plasma

A human growth factor 4-plex panel (Invitrogen; Cat No. LHC0007) was employed to determine various growth factor levels within CBP (n=20) and ABP/S (n=6) samples in triplicate, following the manufacturer's protocol. All measurements were performed by an investigator blinded to the source of the samples. Levels of VEGF, granulocyte colony-stimulating factor (G-CSF), epidermal growth factor (EGF) and fibroblast growth factor basic (FGF-basic) were determined using the Bio-Rad Bio-Plex® Luminex 200 multiplex assay (BioRad Laboratories Inc., Hercules CA, USA). The Bio-Rad Bio-Plex® 200 software (BioRad Laboratories Inc., Hercules CA, USA) was used to calculate the sample growth factor concentrations accordingly to a standard curve and results were presented as μg/mL.

Viability of MNC hUCB Cultured with Autologous CBP

Cryopreserved MNC hUCB cells (n=4 units) were quickly thawed at 37° C., washed with PBS, and centrifuged at 400 g for 5 minutes. Cell quantity and viability were determined using a hemocytometer. The cells were then re-suspended with phenol-free RPMI-1640 media (Gibco, Dublin, Ireland; Cat. No. 11835030) and plated in a 24-well cell culture plate at a density of $5 \times 10^4$ cells/well. Pre-designated wells were supplemented with 10% of autologous CBP, ABP/S, or fetal bovine serum (FBS) (Gibco, Dublin, Ireland; Cat No. 10438026) upon initial plating in duplicate. Cells were incubated at 37° C. with 5% CO2 for 5 days. Media was changed at 24 hours and 3 days after cell plating. On day 5, cell viability was determined using the LIVE/DEAD viability/cytotoxicity kit (Molecular Probes, Cat No. R37601) accordingly to the manufacturer's instructions. Briefly, the culture media was replaced with 250 μL of fresh PBS in each well. In an equal volume to PBS, LIVE/DEAD working solution (250 μL) was added to each well and incubated at 37° C. for 30 minutes.

After incubation, confocal microscopy images (n=3-4/well, totaling n=16-20/supplement, mainly from the middle of the well) of cell fluorescence were obtained at 10× magnification for cell quantification using the Olympus FluoView 1000 confocal laser scanning microscope (Olympus Corporation of the Americas, Center Valley, PA, USA). Live cells were labelled with green fluorescence through the conversion of non-fluorescent cell-permanent calcein acetoxymethyl to intensely fluorescent calcein by ubiquitous intracellular esterase enzyme activity. Dead cells were identified using ethidium homodimer-1, which enters cells through damaged membranes and produces a red fluorescence upon binding to nucleic acids. Cell counts of live (green) and dead (red) cells were determined using NIH ImageJ software (version 1.46).

Apoptotic Activity of MNC hUCB Cultured with Autologous CBP

Cryopreserved MNC hUCB cells (n=6 units) were quickly thawed at 37° C., washed with PBS, and centrifuged at 400 g for 5 minutes. Cell quantity and viability were determined using a hemocytometer. Cells were then re-suspended with phenol-free RPMI-1640 media and plated in a 96-well culture plate at a density of 2×104 cells/well. Pre-designated wells were supplemented with 10% of either autologous CBP, ABP/S, or FBS upon initial plating in duplicate. Cells were incubated at 37° C. with 5% CO2 for 5 days. Media was changed at 24 hours and 3 days after cell plating. On day 5, the apoptotic activity of the cells was determined using the HT TiterTACS™ Assay kit (Trevigen, Bio-Techne, Minneapolis, MN, USA; Cat No. 4822-96-K) accordingly to the manufacturer's instructions. Briefly, the cells were washed with 200 µL of sterile PBS, then quickly fixed using a 3.7% PBS buffered formaldehyde solution. The cells were washed once more with PBS and then permeabilized with Cytonin™ (50 µL/well). TACS-Nuclease™ (50 µL/well) was then added to designated wells to determine total absorbance. The plate was incubated for 60 minutes at 37° C. following a wash with PBS. The endogenous peroxidase activity was quenched with a 3% hydrogen peroxide solution. The wells were then washed once more with PBS and a 1× TdT labelling buffer reaction mix was added to the wells and incubated at 37° C. for 60 minutes. To stop the labelling reaction, 1× TdT stop buffer was added to the well and incubated for 5 minutes, followed by a wash with PBS. The streptavidin-HRP enzyme solution was then added to the wells and incubated for 10 minutes at RT. After an additional wash with PBS, the TACS-Sapphire substrate solution was added and incubated for 30 minutes at RT with light protection. Stop solution of 0.2N HCl was added to each well and absorbance at 450 nm was measured using a spectrophotometer (SpectraMax Plus 384 microplate reader, Molecular Devices, LLC., San Jose, CA, USA). Results were calculated as the percentage of relative apoptotic absorbance values to maximum absorbance values determined for each culture condition. Cell morphology was observed using phase contrast images (n=6/supplement) obtained at 20× using an Olympus IX70 inverted microscope (Olympus Corporation of the Americas, Center Valley, PA, USA).

Statistical Analysis

Data was presented as mean±SEM Statistical analysis was performed using GraphPad Prism Software version 5 (GraphPad Software, Inc.). The results for MNC hUCB viability and apoptotic activity were evaluated using a one-way ANOVA with Tukey's Multiple Comparison post-hoc test. The results for cytokine and growth factors in CBP were analyzed with a two-tailed t test using same software. A value of $P<0.05$ was considered significant.

Conclusion

In conclusion, the inventors demonstrate the unique protein content in the same CBP samples composed of cytokines and growth factors. The novel in vitro finding of autologous CBP with MNC hUCB demonstrated the trophic capacity of this combination through promotion of cell viability and reduction of apoptotic death. These findings further support the potential of CBP as an independent therapeutic or cell-additive agent in clinical applications for various neurodegenerative diseases.

Example 8—Prophetic Treatment of ALS with Cord Blood Plasma

A human patient diagnosed with amyotrophic lateral sclerosis is presented for treatment. The patient is treated with a therapeutically effective amount of human umbilical cord blood plasma, prepared as described below. The therapeutically effective amount of human umbilical cord blood plasma is administered to the patient via intravenous injection. Improvement is shown in motor behavior after treatment with the cord blood plasma.

To increase improvement in motor behavior, the patient receives additional administrations of the same therapeutically effective amount of human umbilical cord blood plasma as multiple administrations throughout the treatment period. Improvement is shown in motor behavior.

Human umbilical cord blood units are obtained from full-term pregnancies by vaginal delivery and are received within 48 hours of collection. Maternal blood samples, collected as the same time as the cord blood, are tested for infectious disease markers of HIV, hepatitis B and C, syphilis, CMV and HTLV I&II. Human umbilical cord blood (hUCB) units, with maternal blood samples negative for all tested infectious markers, are processed to obtain an autologous CBP fraction and mononuclear cell population as detailed below. Upon receipt, the cord blood units are diluted (1:1) with sterile phosphate buffered saline (PBS) without Mg2+ or Ca2+. The cord blood is then fractionated using the density gradient solution Ficoll (Ficoll-Paque Premium: 1.078 g/mL, Cat. No. 17544202; Millipore Sigma, St. Louis, MO, USA) in the Sepax 2 fully automated cell processing system (Biosafe America Inc., Houston, TX, USA), thus allowing for the sterile collection of both CBP and MNC hUCB from each unit of cord blood. The CBP was further centrifuged at 3000 g for 10 minutes to remove any additional red blood cells. The CBP was then aliquoted and stored at −20° C. CBP is thawed prior to administration to the patient.

Example 9—Prophetic Treatment of ALS with Cord Blood Plasma and hUCBCs

A human patient is diagnosed with ALS and is presented for treatment. The patient is tested to determine if the patient exhibits immune dysfunction as an immune-modulator and/or anti-apoptotic factor. If the patient tests positive for immune dysfunction, the patient is injected intravenously with a composition comprising a therapeutically effective amount of MNCs isolated from hUCBCs in combination with a therapeutically effective amount of umbilical cord blood plasma prepared as described below. Improvement in motor function is shown after treatment with both cord blood plasma as well as hUCBCs. Additional administrations of the therapeutic composition are administered with improvement in motor function exhibited.

Human umbilical cord blood units are obtained from full-term pregnancies by vaginal delivery and are received within 48 hours of collection. Maternal blood samples, collected as the same time as the cord blood, are tested for infectious disease markers of HIV, hepatitis B and C, syphilis, CMV and HTLV I&II. Human umbilical cord blood (hUCB) units, with maternal blood samples negative for all tested infectious markers, are processed to obtain an autologous CBP fraction and mononuclear cell population as detailed below. Upon receipt, the cord blood units are diluted (1:1) with sterile phosphate buffered saline (PBS) without Mg2+ or Ca2+. The cord blood is then fractionated using the density gradient solution Ficoll (Ficoll-Paque Premium: 1.078 g/mL., Cat. No. 17544202; Millipore Sigma, St. Louis, MO, USA) in the Sepax 2 fully automated cell processing system (Biosafe America Inc., Houston, TX, USA), thus allowing for the sterile collection of both CBP and MNC hUCB from each unit of cord blood. The CBP was further centrifuged at 3000 g for 10 minutes to remove any additional red blood cells. The CBP was then aliquoted and stored at −20° C. The MNC hUCB cell numbers and viability were determined using the Vi-CELL Viability Analyzer (Beckman Coulter, Brea, CA, USA). MNC hUCB was then frozen at $5 \times 10^7$ cells per vial using a proprietary cryopreservation media (Saneron CCEL Therapeutics, Inc.) and stored in liquid nitrogen. Prior to administration, MNCs and CBP are thawed and combined into a therapeutic composition for administration to the patient.

In the preceding specification, all documents, acts, or information disclosed do not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall there between.

What is claimed is:

1. A method of increasing umbilical cord blood cell (UCBC) viability and reducing apoptotic UCBC death comprising:
    obtaining or having obtained cord blood from a subject;
    diluting or having diluted the cord blood 1:1 with sterile phosphate buffered saline (PBS) in the absence of $Mg_2^+$ and $Ca_2^+$;
    isolating or having isolated an amount of UCBCs from the diluted cord blood of the subject;
    isolating or having isolated an amount of umbilical cord blood plasma from the diluted cord blood of the subject;
    suspending the UCBCs in phenol-free RPMI-1640 media;
    plating the UCBCs suspended in the phenol-free RPMI-1640 media;
    adding about 10% of the umbilical cord blood plasma to the plated UCBCs suspended in the phenol-free RPMI-1640 media to form a culture media wherein the culture media consists of about 10% of the umbilical cord blood plasma and about 90% of the phenol-free RPMI-1640 media;
    culturing the UCBCs in the culture media for about 5 days; and
    removing the UCBCs from the culture media after about 5 days;
    wherein the UCBC cell viability is at least 79% as compared to a control.

2. The method of claim 1, wherein the UCBCs are a mononuclear cell fraction.

3. The method of claim 1, wherein the UCBCs and the umbilical cord blood plasma are obtained from a human.

* * * * *